US009149222B1

(12) United States Patent
Zets et al.

(10) Patent No.: US 9,149,222 B1
(45) Date of Patent: Oct. 6, 2015

(54) ENHANCED SYSTEM AND METHOD FOR ASSESSMENT OF DISEQUILIBRIUM, BALANCE AND MOTION DISORDERS

(75) Inventors: Gary Zets, Maitland, FL (US); Bruce Mortimer, Maitland, FL (US)

(73) Assignee: Engineering Acoustics, Inc, Casselberry, FL (US)

( * ) Notice: Subject to any disclaimer, the term of this patent is extended or adjusted under 35 U.S.C. 154(b) by 797 days.

(21) Appl. No.: 13/300,428

(22) Filed: Nov. 18, 2011

Related U.S. Application Data

(63) Continuation-in-part of application No. 12/201,778, filed on Aug. 29, 2008, now Pat. No. 8,092,355.

(60) Provisional application No. 61/415,371, filed on Nov. 19, 2010.

(51) Int. Cl.
*A61B 5/16* (2006.01)
*A61B 5/00* (2006.01)
*A61B 5/11* (2006.01)
*A63B 26/00* (2006.01)
*A63B 71/06* (2006.01)

(52) U.S. Cl.
CPC .................. *A61B 5/16* (2013.01); *A61B 5/1114* (2013.01)

(58) Field of Classification Search
CPC ...................... A63B 26/003; A63B 2071/0655; A63B 2220/40; A63B 2220/803; A61B 5/16; A61B 5/4082; A61B 5/1114; A61B 5/112; A61B 2562/0219
USPC ......................................................... 600/595
See application file for complete search history.

(56) References Cited

U.S. PATENT DOCUMENTS

| 5,203,346 | A | * | 4/1993 | Fuhr et al. ...................... 600/594 |
| 5,323,174 | A | * | 6/1994 | Klapman et al. ............... 345/156 |
| 5,891,060 | A | * | 4/1999 | McGregor et al. ............. 600/595 |
| 5,954,674 | A | * | 9/1999 | Fuhr .............................. 600/594 |
| 6,234,982 | B1 | | 5/2001 | Aruin |
| 7,292,151 | B2 | | 11/2007 | Ferguson et al. |
| 7,502,498 | B2 | | 3/2009 | Wen et al. |
| 7,651,224 | B2 | | 1/2010 | Wood et al. |

(Continued)

OTHER PUBLICATIONS

51. Terence Cawthorne, Vestibular Injuries, Proc R Soc Med. Mar. 1946; 39(5): 270-273.

(Continued)

*Primary Examiner* — Sean Dougherty
(74) *Attorney, Agent, or Firm* — Stephen C. Thomas

(57) ABSTRACT

A system and method for providing therapy and assessment utilizing vibrotactile feedback is disclosed. Such treatment is useful for the assessment and treatment of disequilibrium, movement and balance disorders. The system and method measures a subject's performance of predetermined tasks with respect to expected parameters using sensors such as force plates, inertial sensors, and three dimensional cameras. Predetermined motions are motions such as stand, sit-to-stand, reach, bend, functional gait, functional gait plus head-shake, and other functional tasks. Vibrotactile stimulation may be applied during the subject's performance as disruptive input. Variance and rate of change of variance between measured and expected parameters is used as a tool for assessment of said subject, and is also used for providing real-time vibrotactile training to said subject. The invention is useful in the treatment of Traumatic Brain Injury (TBI), neurologic disorders causing disequilibrium and balance disorders, and the like.

19 Claims, 15 Drawing Sheets

(56) References Cited

U.S. PATENT DOCUMENTS

| | | | |
|---|---|---|---|
| 7,952,483 B2 | 5/2011 | Ferguson et al. | |
| 8,092,355 B2* | 1/2012 | Mortimer et al. | 482/142 |
| 2006/0005846 A1 | 1/2006 | Krueger et al. | |
| 2006/0056655 A1 | 3/2006 | Wen et al. | |
| 2007/0093989 A1* | 4/2007 | Nashner | 702/185 |
| 2007/0121066 A1 | 5/2007 | Nashnew | |
| 2007/0204687 A1 | 9/2007 | Haselhurst et al. | |
| 2008/0234113 A1 | 9/2008 | Einav | |
| 2010/0049095 A1* | 2/2010 | Bunn et al. | 600/595 |
| 2010/0156653 A1 | 6/2010 | Chaudhari | |
| 2011/0054870 A1 | 3/2011 | Dariush et al. | |
| 2011/0098608 A1* | 4/2011 | Griffiths et al. | 600/595 |
| 2011/0143868 A1 | 6/2011 | Marty et al. | |
| 2011/0212810 A1 | 9/2011 | Jeka et al. | |

OTHER PUBLICATIONS

U.S. Appl. No. 12/201,778, filed Jan. 10, 2012, Bruce J.P. Mortimer.
Berg KO, Wood-Dauphinee S. Williams JI & Gayton D, Measuring balance in the elderly: preliminary development of an instrument. 1989, Physiotherapy Canada 41: 304-311.
Nashner LM, Strategies for organization of human posture. In: Igarashi, black, Vestibular and visual control on posture and locomotor equilibrium. 1985, Basel, New York pp. 1-8.
Kuo AD, An optimal control model for analyzing human postural balance. 1995, IEEE Trans Biomed Eng 42: 87-100.
Nashner LM & McCollum G, The organization of human postural movements: A formal basis and experimental synthesis. 1985, Behav Brain Sci. 8: 135-172.
Samer S. Hasan, Deborah W. Robin, and Richard G Shiavi, Drugs and Postural Sway, IEEE Engineering in Medicine and Biology, 1992.
John Jeka, Kelvin Oie, Gregor Schoner, Tjeerd Dijkstra, and Elaine Henson, Position and Velocity Coupling of Postural Sway to Somatosensory Drive JN 1661-1674, 1998.
Merlo, J.L., Stafford S.C., Gilson, R. & Hancock, P.A. (2006), The effects of physiological stress on tactile communication. Proceedings of the Human Factors and Ergonomics Society 50th Annual Meeting, San Francisco, CA.
Bruce J.P. Mortimer, Gary A. Zets, and Roger W. Cholewiak, "Wibrotactile transduction and transducers" Journal of the Acoustic Society of America, 121(5) 2970-2977, May 2007.
Patrick D. Roberts and Gin McCollum, Dynamics of the sit-to-stand movement, Biological Cybernetics, vol. 74, No. 2 / Jan. 1996.
Kuo AD (2005), State estimation model of sensory integration in human postural balance, J. Neural Eng., S235-S249.
Huxham F et al. 2001. Theoretical considerations in balance assessment. Australian Journal of Physiotherapy 47: 89-100.
Anne Shumway-Cook and Marjorie Woollacott, Motor Control, 2nd Ed, Lippincott Williams and Wilkins, 2001.
Susan Herdman, Vestibular Rehabilitation 3rd Ed, Contemporary Perspectives in Rehabilitation 2007.
L.M. Nashner, M. Woollacott, and G. Tuma, Organization of Rapid Responses to Postural and Locomotor-like Perturbations of Standing Man, Exp. Brain Res. 36, 463-476 (1979).
Hanson, James V.M.;Whitaker,David;Heron, James, Preferential processing of tactile events under conditions of divided attention, Neuroreport:10/7/09—vol. 20, Iss 15,p. 1392-1396.
Marc O. Ernst & Martin S. Banks, Humans integrate visual and haptic information in a statistically optimal fashion, Nature, vol. 415, Jan. 24, 2002.
Kolb B, Gibb R, Robinson T. 2003. Brain plasticity and behavior. Current Directions in Psychological Science 12:1-5.
Classen J, Liepert J, Wise S, Hallen M, Cohen L. 1998. Rapid Plasticity of human cortical movement representation induced by practice. Journal of Neurophysiology 79:1117-23.
J. Milton, J.L.Cabrera, T.Ohira, S.Tajima, Y.Tonosaki, C.W.Eurich, S.A.Campbell, 2009.The Time-delayed inverted pendulum:Implications for human balance control. Chaos 19: 026116.
Lorenzo Chiari, Marco Dozza, Angelo Cappello, Fay B. Horak, Velio Macellari, and Danielle Giansanti, Audio-Biofeedback for Balance Improvement: An Accelerometry-Based system, IEEE Transactions on Biomedical Engineering, vol. 52, No. 12, Dec. 2005.
Allum, John; Davis, Justin; Carpenter, Mark, Meyes, Simon; Tschanz, Roger; Debrunner Daniel; Burger Juergen, Prosthetic device based on multi-modal feedback improves balance control for the healthy young and elderly. ISPGR 2007.
E. Bruce Goldstein, Ecology of J.J. Gibson, Leonardo, vol. 14, No. 3 (Summer, 1981), pp. 191-195.
Michael Young, An Ecological Psychology of Instructional Design: Learning and Thinking by Perceiving—Acting Systems, In D. Johanassen, (Ed.), Handbook of research on educational communications and technology (2nd ed., pp. 169-177), Mahwah, NJ: Lawrence Erlbaum Associates. Ecological Psychology of Instructional Design, 2004.
C Wickens, Multiple resources and performance prediction, Theoretical Issues in Ergonomic Science, 3(2):159-177, 2002.
Liepert J, Bauder H, Wolfgang HR, Miltner WH, Taub E, Weiller C. Treatment-induced cortical reorganization after stroke in humans. Stroke. 2000;31:1210-1216.
28. M Hoffer, K Gottshall, B Balough, C Balaban, Vestibular Difference Between Blast and Blunt Head Trauma, ARO, Abstract 50, Feb. 20, 2008.
M. Scherer and M Schubert, Traumatic Brain Injury and Vestibular Pathology as a Comorbidity After Blast Exposure, Phys Ther. vol. 89, No. 9, Sep. 2009, pp. 980-992.
Lawson, B.D., & Rupert, A.H. (2010). Vestibular aspects of head injury and recommendations for evaluation and rehabilitation following exposure to severe changes in head velocity or ambient pressure. Peer-Reviewed Proceedings of the International Conference on Human Performance at Sea (HPAS), University of Strathclyde, Glasgow, U.K., Jun. 16-18, pp. 367-380. Edited by O. Turan, J. Bos, J. Stark, & J. Colwell. ISBN: 978-0-947649-73-9.
J Honaker, C Conversey N Shepard, Modified Head Shake Computerized Dynamic Posturography, American Journal of Audiology • vol. 18 • 108-113 • Dec. 2009.
33. Marco Dozza, Biofeedback Systems for Human Postural Control, Università Di Bologna, PhD Thesis, 2007.
Sienko et al., Assessment of Vibrotactile Feedback on Postural Stability During Pseudorandom Multidirectional Platform Motion, IEEE Transactions on Biomedical Engineering, vol. 57, No. 4, Apr. 2010.
Wall III C, Kentala E. 2005. Control of sway using vibrotactile feedback of body tilt in patients with moderate and severe postural control deficits. Journal of Vestibular Research 15: 313-25.
Wrisley D. 2007. Vision of balance rehabilitation. Presented at A Paradigm Shift: Technology based intervention improving outcomes for dysequilibrium, dizziness, mobility, balance, and falls, Celebration, Florida, USA.
Karen Atkins, PhD Research Study, Nova South Eastern Univ. 2009.
Davilov YP, Tyler ME, Skinner KL, Hogle RA, Bach-y-Rita P. Efficacy of electrotactile vestibular substitution in patients with peripheral and central vestibular loss. Journal of Vestibular Research. 2007; 17(2-3):119-130.
Dozza, Marco; Wall III, Conrad; Peterka, Robert J.;Chiari, Lorenzo; Horak, Fay B. Effects of Practicing Tandem Gait with and without Trunk-Tilt Biofeedback in Subjects with Unilateral Vestibular Loss, J Vestib Res. 2007;17(4):195-204.
C.G. Danis, D.E. Krebs, K.M. Gill-Body and S. Sahrmann, Relationship between standing posture and stability, Phys Ther 78 (1998), 502-517.
Tee LH, Chee NW. Vestibular rehabilitation therapy for the dizzy patient. Ann Acad Med Singapore 2005;34:289-94.
P. Kadkade, B. Benda, P. Schmidt, and C Wall, IIIVibrotactile Display Coding for a Balance Prosthesis, IEEE Transactions on Neural Systems and Rehabilitation Engineering , vol. 11, No. 4, Dec. 2003, 392-399.
John Jeka, Tim Kiemel, Robert Creath, Fay Horak and Robert Peterka, Controlling Human Upright Posture: Velocity Information Is More Accurate Than Position or Acceleration, J Neurophysiol 92:2368-2379, 2004.
K Gottshall, Tracking recovery of vestibular function in individuals with blast-induced head trauma using vestibular-visual-cognitive interaction tests, JNPT, 34, 2010.

(56) References Cited

OTHER PUBLICATIONS

F. B. Horak, Postural orientation and equilibrium: what do we need to know about neural control of balance to prevent falls? Age and Ageing 2006; 35-S2.

Huang H, Wolf SL, He J. Recent developments in biofeedback for neuromotor rehabilitation. J Neuroeng Rehabil. Jun. 21, 2006;3:11.

Erik E. Stone and Marjorie Skubic, Passive In-Home Measurement of Stride-to-Stride Gait Variability Comparing Vision and Kinect Sensing, 33rd Annual International Conference of the IEEE EMBS, Boston, Massachusetts USA, Aug. 30-Sep. 3, 2011.

Mortimer B, Zets G, Mort G and Shovain C, Implementing Effective Tactile Symbology for Orientation and Navigation, 14th International Conference on Human Computer Interaction, HCI (2011).

Microsoft Kinect for windows sdk, 2011 http://research.microsoft.com/en-us/um/redmond/projects/kinectsdk/.

F. S. Cooksey, Rehabilitation in Vestibular Injuries, Proc R Soc Med. Mar. 1946; 39(5): 273-278.

* cited by examiner

ENHANCED SYSTEM AND METHOD FOR ASSESSMENT OF DISEQUILIBRIUM, BALANCE AND MOTION DISORDERS

CROSS REFERENCE TO RELATED APPLICATIONS

This application claims the benefit of provisional patent application Ser. No. 61/415,371, filed with the USPTO on Nov. 19, 2010, which is herein incorporated by reference in its entirety this application is also a Continuation In Part and claiming the benefit of U.S. application Ser. No. 12/201,778, filed Aug. 29, 2008, now U.S. Pat. No. 8,092,355 which issued on Jan. 10, 2012 and which is also incorporated herein by reference in its entirety.

STATEMENT REGARDING FEDERALLY SPONSORED RESEARCH OR DEVELOPMENT

Funded under contract W81XWH-10-C-0155 Treatment of mTBI Balance Dysfunction via Multimodal Biofeedback US SBIR.

INCORPORATION-BY-REFERENCE OF MATERIAL SUBMITTED ON A COMPACT DISK

Not applicable.

BACKGROUND OF THE INVENTION

1. Field of the Invention

The present invention relates generally to systems and methods for providing assessment of a subject with disorders such as disequilibrium, balance or motion disorders and, more particularly, to a system and method for providing assessment by measuring a subject's performance of predetermined tasks and comparing said performance with expected parameters associated with said tasks.

2. Background of the Invention

Balance, or a state of equilibrium, may be described as the ability to maintain the body's position over its base of support. In particular, the optimal posture for controlling balance typically requires maintaining the body's center of gravity (COG) within the base of support, such as the support frames defined by the foot soles. Balance may be divided into static balance and dynamic balance, depending on whether the base of support is stationary or moving. Dynamic balance, even during voluntary movements, is particularly complex task for humans; stability depends on the kinetics, motor control, sensory information, neuro processing delays and environmental conditions. Ambulation such as exemplified with walking gait, requires anticipatory, reflex and voluntary control of a multi-dimensional biomechanical system, yet is a task that healthy adult humans do with ease.

Disequilibrium and movement and balance disorders can be debilitating and increase the potential for falls. A movement disorder is a condition that prevents normal movement. Some movement disorders are characterized by lack of controlled movement, and while others are characterized by excessive movement. A balance control disorder is typically the result of sensory and/or motor disorders which impair equilibrium control by a subject. Balance control disorders may be bilateral, i.e., affect a subject on both left and right sides, or may only be manifested on one side. Movement and balance disorders may be caused by disorders in the vestibular, somatosensory, or central or peripheral nervous systems.

The vestibular system carries sensory information related to body equilibrium, specifically roll, pitch, and yaw motion oriented relative to the direction of gravity. Information is generated by the semicircular canals and maculae in the inner ear, relayed by the vestibular nerve to the brainstem vestibular nuclei, and processed by the vestibular nuclei and mid brain with corresponding muscular contraction and relaxation known as motor output.

Aspects of the somatosensory system include: 1) perception of pressure, vibration, and texture, i.e., discriminative touch, 2) perception of pain and temperature, and 3) proprioceptive sensation. Proprioception, which is often referred to more generally as the somatosensory system, involves awareness of movement derived from muscular, tendon, and joint articular surfaces provided by the peripheral nervous system and processed in the parietal lobe of the brain. These interoception senses provide internal feedback on the status of the body, indicating whether the body is moving with required effort and indicating where various parts of the body are located in relation to each other. Thus, proprioception involves the essential stimuli provided to, or received by, skin, joints, and/or muscles to maintain equilibrium or balance control.

Damage to any part of the central or peripheral nervous systems may interfere with balance control. Central nervous system processing includes the brain primary motor cortex responsible for generating the neural network impulses controlling execution of movement, the posterior parietal cortex responsible for transforming visual information into motor commands, the premotor cortex responsible for sensory guidance of movement and control of proximal and trunk muscles of the body, and the supplementary motor area responsible for planning and coordination of complex movements such as coordinated activity using limbs.

In particular, vision plays a significant role in balance. Indeed, up to twenty percent of the nerve fibers from the eyes interact with the vestibular system. A variety of visual dysfunctions can cause disequilibrium. These dysfunctions may be caused directly by problems in the eyes, or may be caused indirectly by disorders related to stroke, head injury, vestibular dysfunction, deconditioning, decompensation, or the like.

Meanwhile, the peripheral nervous system generally relates to the conduction of sensory information, or messages, from the peripheral nerves to the brain and spinal cord. For example, such sensory information may indicate that there is a pressure on the sole of a foot or that a toe is flexed. Sensory information may also indicate that the feet are cold or that a finger is burned.

Accordingly, the body relies on the interaction of several systems to control movement, balance, and posture. For example, the vestibular system in the ears orient upright stance, especially when the eyes are closed. The cutaneous, proprioceptive sensory system feels pressure under the feet. In addition, the joint and muscle spindles are sensitive to joint position and movement. Moreover, cognition or brain processing estimates the motor response magnitude. In sum, balance disorders are predominantly multi-causal with imbalance occurring due to deficits in more than one sensory, motor, neuro or cortical pathway.

Traumatic brain injury (TBI) or mild traumatic brain injury (mTBI), occurs when physical trauma causes temporary or permanent neurological damage. mTBI typically involves temporary impairment of neurological function which usually quickly resolves by itself, and conventional neuroimaging normally shows no gross structural changes to the brain as the result of the condition. Overt symptoms may often include balance (M. Scherer and M Schubert, Traumatic Brain Injury and Vestibular Pathology as a Comorbidity After Blast Exposure, PHYS THER. Vol. 89, No. 9, September 2009, pp. 980-992) and spatial disorientation problems (vertigo) related to vestibular dysfunction, vision disturbances, inner-ear edema, and/or other sensory integration deficits. Treatment of this particular population group has several challenges which include: early and specific injury assessment, the determination of appropriate return-to-duty measures and selection of effective individualized balance rehabilitation and treatment tools. The group is also highly variable in the nature and extent of balance deficits and cognitive and/or related psychological impairments but it appears that almost all subjects show some susceptibility to vestibular or vestibular/ocular disorders.

The cause and extent of any deficits in a subject's movement and balance control may, in prior art, be determined by assessing the subject's ability to control movement and balance while performing a number of standard functional motor tasks, such as standing still, moving from a sitting position to a standing position, walking, walking on steps and uneven surfaces, or the like. This assessment may also be achieved by manipulating sensory input and monitoring motor response. Quantified sensory assessment, for example, may examine touch-pressure, two-point discrimination, inner ear response to warm and cold, or visual acuity by reading the print on an eye chart. Diagnosis may also be determined qualitatively according to the observations by an examining physician or a physical therapist.

There is a clear need for objective measurements both to assess the patient's original deficit and their rate of progress through rehabilitation. Therefore data capture and analysis, even while completing therapeutic activities (for example during functional movement tasks) can be used to provide information to the therapist, optimize motional limit tasks and adaptively alter feedback settings and motional task difficulty. In particular, certain functional gait tasks are known in prior art to be reliable and accurate indicators of behavior functional ability. However, previous efforts to measure performance during functional gait tasks rely on human observations and subjective scoring.

The system and method of the invention is useful for achieving objective assessment of patient deficit, and is also useful for providing therapeutic training. As further described below, the use of three dimensional cameras to measure variance and rate of change of variance is a particularly novel aspect of the system and method of the present invention. Furthermore, the combining of multi-sensor signals which include both inertial and three dimensional camera measurements, or, in yet a further embodiment of the system and method of the invention the combining of inertial, three dimensional camera, and force plate measurements, to quantify variance and rate of change of variance is also a particularly novel aspect of the invention. There are other aspects of the invention as described herein that are novel and non-obvious relative to the prior art.

After a balance deficit has been assessed and quantified using the system and method of the invention, a physician may prescribe remedial measures to try and bring the subject's balance control near or within normal limits. In certain instances, the physician may prescribe medication that reduces the action of peripheral senses on the brain or enhance neural network function. Alternatively, the physician may prescribe a course of physical therapy, which will typically last at least several months, with the object of training the subject's brain to deal with a reduced sense of balance when trying to maintain the body upright and prevent a fall. Normally, neither of these techniques will have an immediate effect on the subject's balance deficit. Moreover, medication can have side effects, and can also reduce the capability of the brain to process balance information from the peripheral senses. A traditional course of physical therapy requires a long training period which may extend over more than two months. These difficulties and limitations associated with conventional remedial measures for dealing with balance deficits are most problematic when the subject has suffered a blast related head injury, or is older and likely to have a falling tendency.

BRIEF SUMMARY OF THE INVENTION

The present invention comprises a system and/or method that have one or more of the following features and/or steps, which alone or in any combination may comprise patentable subject matter.

In view of the foregoing, there is a need for a system and a method for rehabilitating disequilibrium and movement and balance disorders, and a system and method for the assessment of balance dysfunction that is based upon objective measurements. The present invention provides systems and methods for providing motional training to a subject and treatment of balance disorders by providing the subject with vibrotactile feedback in response to the variance, or the rate of change of variance, between the expected parameters associated with a predetermined tasks and the actual performance of the subject; furthermore, the present invention provides systems and methods for providing objective assessment of disequilibrium and balance disorders.

The system and method of the invention utilizes sensors of various types to perform measurements on a subject while that subject attempts to perform a predetermined task, or tasks, which have at least one parameter. The sensors of the system and method of the invention measure the variance between the parameter (the expected value) and the actual performance of the subject (the measured value). The sensors of the system and method of the invention may be any sensor that is configured to measure movement, position, weight, pressure, or the like. Examples of such sensors are force plates comprised of sensors providing a signal relative to the force applied; three dimensional (3D) cameras capable of resolving distance to an object and providing a signal relative to this distance; and inertial sensors capable of measuring change of inertia and which are configured to provide signals relative to such changes. Other sensors as are known in the art to measure movement, position, weight, orpressure, are also within the scope of this disclosure. Each of the sensors contemplated in the method and system of the invention has associated with it a sensing field for which the sensor performs its sensing function and provides signals relative to the sensed parameter. For instance, the sensing field of a force plate is the surface area of the plate over which force measurements are sensed by the force plate. Likewise, the sensing field of a three dimensional camera is the field of view in which the camera performs optical measurements. Also, the sensing field of an inertial sensor is body to which the inertial sensor is attached and for which the inertial sensor provides signals whenever there is movement of the body being sensed. The embodiments of the system and method of the invention may comprise at least one sensor of any type, or may comprise sensors of various type, in any combination, or number. The number and type of sensor is not intended to be a limitation on the scope of the system and method of the invention.

In all embodiments described herein, the rate of change of variance may also be utilized in the system and method of the invention. The rate of change of variance may be used exclusively or may also be used in combination with the variance to assess the subject as described herein, or to provide input to the vibrotactile actuators which are used to train the subject.

At least one preferred embodiment of the system and method of the invention provides a method for providing motional training and therapy to a subject, comprising: determining at least one predetermined task for a subject to perform, said predetermined task characterized by having at least one parameter having an expected value for objective measurement; positioning the subject with the sensing field of at least one sensor; monitoring an attempt by the subject to perform the at least one predetermined motion, the act of monitoring including receiving sensor signals from the at least one sensor capable of producing sensor signals; the sensor signals indicating a variance, rate of change of variance, or both, between the expected parameter and the actual performance of the subject in attempting to perform the at least one predetermined task; providing vibrotactile signals to the subject by activating one or more actuators coupled to the subject, the one or more actuators being spatially oriented with respect to the subject to indicate one or more directions and indicating the variance, rate of change of variance, or both, with respect to the one or more directions; and training the subject according to the vibrotactile signals to minimize the variance while the subject performs the at least one predetermined motion.

Another embodiment of the system and method of the invention provides a system for providing motional training to a subject, comprising: one or more force plates that support a subject and provides force-plate-sensor signals while the subject performs at least one predetermined task, the force-plate-sensor signals indicating the results of the attempt by the subject to perform the at least one predetermined task; and one or more actuators that are configured to be coupled to the subject and that provide vibrotactile feedback to the subject indicating a variance, or rate of change of variance, or both, with respect to one or more directions, between the at least one predetermined motion and the results of the attempt by the subject to perform the at least one predetermined motion, the one or more actuators being spatially oriented with respect to the subject to indicate the one or more directions. This embodiment may further comprise one or more inertial sensors that are configured to be coupled to the subject and provide inertial-sensor signals while the subject performs the at least one predetermined task, the inertial-sensor signals further indicating the variance. This embodiment may also further comprise one or more three dimensional cameras that are configured to measure the performance of the subject while the subject performs the predetermined task, from which the variance or rate of change of variance, or both, can be measured.

Another embodiment provides a system and method for providing motional training to a subject, comprising: one or more sensors that provide respective postural signals while the subject performs at least one predetermined task having a parameter for which there is an expected value, the sensor signals indicating the results of the attempt by the subject to perform the at least one predetermined task; and one or more actuators that are configured to be coupled to the subject and that provide vibrotactile feedback to the subject indicating a variance or rate of change of variance, or both, with respect to one or more directions, between the at least one predetermined motion and the results of the attempt by the subject to perform the at least one predetermined motion, the one or more actuators being spatially oriented with respect to the subject to indicate the one or more directions. The embodiment may further comprise one or more sensors that are configured to be coupled to the head of the subject and provide head orientation signals while the subject performs the at least one predetermined motion, the sensor signals further measuring and indicating the results of the attempt by the subject to perform the at least one predetermined motion.

Another embodiment provides a system and method for providing motional training to a subject during locomotion and gait, comprising: one or more sensors that provide respective postural signals while the subject performs at least one predetermined motion, the sensor signals indicating the results of the attempt by the subject to perform the at least one predetermined motion; and one or more actuators that are configured to be coupled to the subject and that provide vibrotactile feedback to the subject indicating a variance or rate of change of variance, or both, with respect to one or more directions, between the at least one predetermined motion and the results of the attempt by the subject to perform the at least one predetermined motion, the one or more actuators being spatially oriented with respect to the subject to indicate the one or more directions.

Another embodiment provides a system and method for the optimum calculation of the variance and rate of change of variance, with respect to one or more directions, between the at least one predetermined motion and the results of the attempt by the subject to perform the at least one predetermined motion, the one or more actuators being spatially oriented with respect to the subject to indicate the one or more directions.

Another embodiment provides a system and method for providing motional training to a subject, comprising: one or more 3D camera sensor systems that measure the location and orientation of a subject and provides signals while the subject performs at least one predetermined motion, the 3D camera sensor signals indicating the results of the attempt by the subject to perform the at least one predetermined motion; and one or more actuators that are configured to be coupled to the subject and that provide vibrotactile feedback to the subject indicating a variance, or rate of change of variance, or both, with respect to one or more directions, between the at least one predetermined motion and the results of the attempt by the subject to perform the at least one predetermined motion, the one or more actuators being spatially oriented with respect to the subject to indicate the one or more directions.

Another embodiment provides a system and method for providing motional training to a subject, comprising: one or more 3D camera sensor systems that measure the location and orientation of biomechanical features of a subject such as arms, legs, torso, head, feet and provides signals while the subject performs at least one predetermined motion, the 3D camera sensor signals indicating the results of the attempt by the subject to perform the at least one predetermined motion; and one or more actuators that are configured to be coupled to the subject and that provide vibrotactile feedback to the subject indicating a variance, or rate of change of variance, or both, with respect to one or more directions, between the at least one predetermined motion and the results of the attempt by the subject to perform the at least one predetermined motion, the one or more actuators being spatially oriented with respect to the subject to indicate the one or more directions.

Another embodiment provides a system and method for assessing the motional functional ability of a subject, comprising: one or more sensors that provide respective postural signals while the subject performs at least one predetermined motion, the sensor signals indicating the results of the attempt by the subject to perform the at least one predetermined motion; the steps of narrowing the subjects base of support and stepping heel to toe along a defined axis, the steps of requiring and guiding simultaneous, continuous head movement to predefined limits and rates during stepping, providing auditory feedback when said limits have been reached and recording data from the predetermined motion for analysis and score.

These and other aspects of the present invention will become more apparent from the following detailed description of the preferred embodiments of the present invention when viewed in conjunction with the accompanying drawings.

It is understood that although aspects of the present invention may be described with respect to the treatment of balance disorders, embodiments may be applied more generally to any type of motional training. It should also be evident that the systems and methods described herein may be used for non-medical activities such as sports, dance, or specific work task training.

BRIEF DESCRIPTION OF THE DRAWINGS

The accompanying drawings, which are incorporated into and form a part of the specification, illustrate one or more embodiments of the present invention and, together with the description, serve to explain the principles of the invention. The drawings are only for the purpose of illustrating the preferred embodiments of the invention and are not to be construed as limiting the invention. In the drawings.

DETAILED DESCRIPTION OF THE INVENTION

Figure 1:
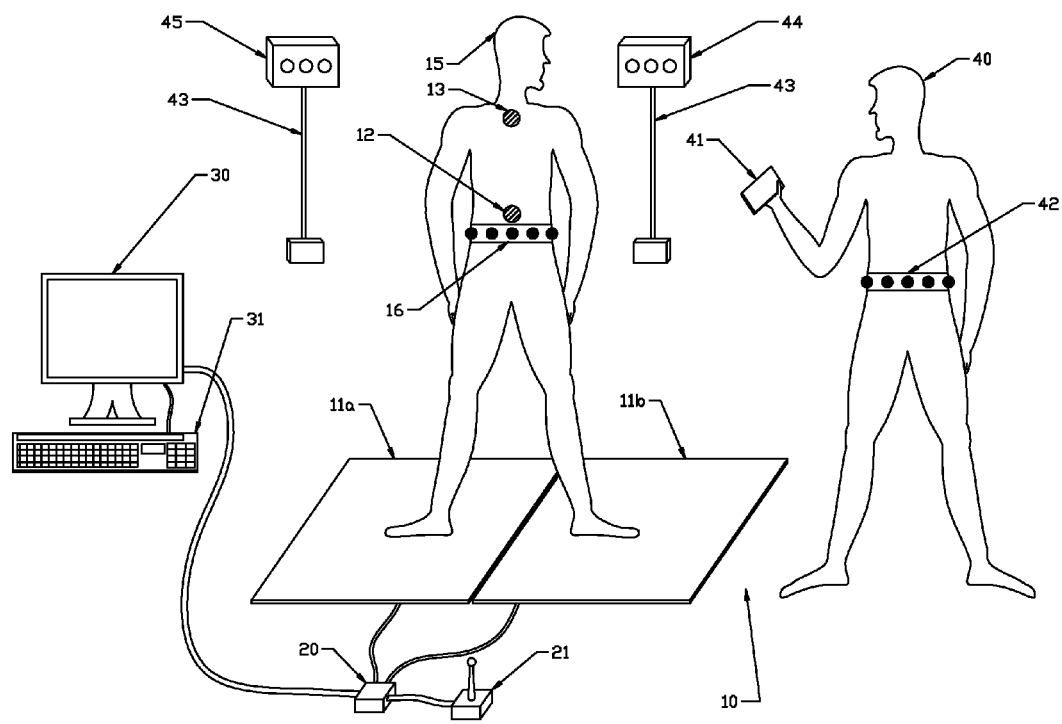
FIG. 1 illustrates an embodiment of a motional training system according to aspects of the present invention.

The following documentation provides a detailed description of the invention.

Although a detailed description as provided in the attachments contains many specifics for the purposes of illustration, anyone of ordinary skill in the art will appreciate that many variations and alterations to the following details are within the scope of the invention. Accordingly, the following preferred embodiments of the invention are set forth without any loss of generality to, and without imposing limitations upon, the claimed invention. Thus the scope of the invention should be determined by the appended claims and their legal equivalents, and not merely by the preferred examples or embodiments given.

Embodiments according to aspects of the present invention provide systems and methods for providing a subject with assessment or motional training, or both. In particular, embodiments provide motional training by providing a subject with vibrotactile feedback in response to an attempt by the subject to perform predetermined motions.

The set of predetermined tasks may correspond to a functional task, while each predetermined motion corresponds to a sub-task. The act of moving from a sitting position to a standing position is a known and well documented functional task. Other examples include standing, reaching for an object, getting out of bed, and tasks related to gait.

The embodiments provide spatial orientation and/or timing feedback cues via a vibrotactile mechanism to guide postural and mobility decisions. Real time vibrotactile feedback may be provided to cue appropriate motions by the subject. In addition, such feedback may also be used to correct abnormal movement that can occur during functional tasks. Unlike the prior art, the embodiments recognize that sensory feedback requirements are context sensitive, and thus employ vibrotactile stimulation that may vary by type, location, duration, etc. to provide information that relates closely to each stage of a the functional activity. Thus, in some embodiments, the vibrotactile feedback is provided according to specific, and often well-understood, sub-tasks, thereby restricting the context and simplifying the control intelligence.

For example, the approaches to motional training described herein may be employed to treat balance disorders.

Subjects with balance disorders may be trained to perform basic functional tasks and sub-tasks, so that the subjects learn balance strategies and retain the skills needed to prevent falls. In general, aspects of the present invention take advantage of the brain's ability to re-organize and re-learn the functional tasks and sub-tasks. Thus, embodiments provide a tool by which a subject and a therapist may determine the limits of stability and understand how the subject can learn/relearn functional tasks and sub-tasks.

In addition, embodiments allow such tasks to be scripted from a set of defined sub-tasks tailored to a subject. In other words, embodiments provide for the design of new tasks or the concatenation of different sub-tasks together to define more complex tasks. Of particular interest are functional activities that involve transitional motion, i.e., the change from one motional condition to another. For example, the sit-to-stand task includes several sub-tasks: sit, upper body lean, transition to upright stance, and steady upright stance. The sequence from one stage to the next is transitional and thus requires well bounded temporal (timing) and spatial (kinematical) conditions to be achieved.

Moreover, because the object of clinical treatment is the transfer of knowledge and experience to the subject during the treatment, embodiments facilitate dynamic modifications to accommodate the special needs of each subject and to adapt dynamically to challenge the subject to achieve new skill levels when the subject has mastered a certain tasks. This dynamic process is believed to be related to brain plasticity. Thus functional activities, after a training and evaluation period, may be repetitively practiced in a clinical setting using an environment that adaptively changes task difficulty as well as the number of tasks. Some embodiments also contemplate a take-home system that is programmed with the characteristics and requirements tailored to specific subjects, at a specific stage in their training or treatment, allowing subjects to continue balance training therapy in the home environment.

Referring now to FIG. 1, a motional training system 10 according to aspects of the present invention is illustrated. The motional training system 10 is operated by a therapist 40 to provide motional training for a subject 15. As described previously, in an example application, the motional training system 10 may be employed to treat balance disorders in the subject 15. As shown in FIG. 1, the subject 15 is situated on force plates 11a and 11b, while a vibrotactile feedback mechanism 16 as well as optional inertial sensors 12 and 13 are mounted on, or coupled to, the subject 15. Meanwhile, another vibrotactile feedback mechanism 42 may be mounted on the therapist 40.

In general, the motional training system 10 may be operated with an intelligent controller 20, which may be any processing device, such as a conventional desktop computer, that can execute programmed instructions (or system software) provided on media well known in the art such as any computer-readable memory. A visual display monitor 30 and an optional keyboard interface 31 may be connected to the intelligent controller 20 to provide a user interface. The therapist 40 may also operate aspects of the motional training system 10 via a remote interface 41 as shown in FIG. 1. The remote interface could be a touch screen, keypad or the like, connected via a wireless or wired interface to the intelligent controller 20. The force plates 11a and 11b, the vibrotactile feedback mechanism 16, and the inertial sensors 12 and 13 may communicate with the intelligent controller 20 via conventional wired or wireless connections. For example, the force plates 11a and 11b may communicate directly to the intelligent controller 20 using a wired connection, such as a conventional universal serial bus (USB) connection or the like. Meanwhile, a wireless data connection 21, such as Bluetooth or the like, shown in FIG. 1 may allow the intelligent controller 20 to communicate with the vibrotactile feedback mechanism 16 and the inertial sensors 12 and 13. In addition, the remote interface device 41 may also use a wireless interface to connect to other components of the motional training system 10. In general, wireless communications may be particularly suitable for components of the motional training system 10 that must move easily with the subject 15 or the therapist 40; however, it is not required that these connections are wireless. The form of electrical communication between the components of the system of the invention may take any form well known in the art such as wired, wireless optical, or any other form and is not to be construed as a limitation of the scope of the claims herein In other embodiments, the components (visual display monitor 30, intelligent controller 20, keyboard interface 31 and wireless data connection 21) may be integrated within one composite unit, for example a touch-screen all-in-one computer.

The force plates 11a and 11b provide a technique for measuring body sway in terms of displacement of the center of foot pressure (COP), generated by the inherent instability of the subject 15 standing on the fixed support surface of the force plates 11a and 11b. The COP is computed from the signals provided by force transducers which are typically embedded in the corners the force plates 11a and 11b. The force transducer outputs are processed to obtain a projection of the resultant forces acting at the subject's center of gravity (COG) via the force plates 11a and 11b.

In general, a force plate is a sensor that measures the load at discrete points mounted beneath a relatively rigid plate. The load is usually measured using load-cell type sensors, converted into an electronic voltage signal and sampled using an analog to digital converter to be in a form suitable for computer or microcontroller processing. The response from one or multiple force plates can be combined using known analog to digital and mathematical algorithms implemented in computer software. The load cells and measurement conversion electronics in the embodiment of FIG. 1 may be configured to be accurate for a range of subject weights, for example from approximately 100 to approximately 300 pounds. While this configuration is a typical force plate configuration, it is not to be construed as a limitation on the claims. Any mechanism using means known in the art to provide the above signals is conceived to be within the scope and breadth of the claims herein.

Although the embodiment of FIG. 1 illustrates two force plates 1a and 11b positioned adjacent to each other to form a combined area, any number or configuration of force plates may be employed to produce an active area that is sufficiently large to support the subject 15 while standing and/or performing predetermined motions as described further below. For example, the combined area of the force plates 11a and 11b may be greater than approximately 20 inches by approximately 11 inches.

Although the sensors used in some embodiments may be limited to the use of force plates 11a and 11b, the embodiment of FIG. 1 also employs the optional inertial sensors 12 and 13. As illustrated in FIG. 1, the inertial sensor 12 may be mounted proximate to the center of gravity (COG) of the subject 15, i.e., in the area of the lower back of the subject 15. The inertial sensor 12 may be mounted according to any suitable arrangement. For example, the inertial sensor 12 may be incorporated with a belt or garment worn by the subject 15. Alternatively, the inertial sensor 12 may be incorporated into the vibrotactile feedback mechanism 16 worn by the subject 15. Meanwhile, the optional additional inertial sensor 13 may be mounted higher on the upper body of the subject 12, for example at the back of the neck proximate to the top of the spine. The inertial sensor 13 may be incorporated in a garment or accessory worn by the subject 15. Accordingly, the inertial sensor 12 provides information regarding the orientation and motion of the COG, while the inertial sensor 13 second sensor provides information regarding the orientation and motion of the upper body of the subject 15.

Commercially available inertial sensors are typically provided with on-board intelligent processing, real-time signal filtering, and digital interfacing. In particular, each inertial sensor 12 or 13 may be a three-axis device that employs accelerometers and magnetometers. In some embodiments, the three-axis device may combine three-axis accelerometers with a magnetometer to provide a tilt sensor. In other embodiments, the three-axis device may employ gyroscopes to provide higher resolution than the tilt sensors, which are angular rate limited due to filtering and may be prone to drift.

The choice of sensor is typically based on resolution and costs constraints. For example, the measurement of spine angle during a sit to stand transition will require less resolution in clinical systems where the primary body orientation is measured using a force plate sensor. In this example, an accelerometer or low cost inertial device will provide sufficient accuracy for this task. However, for a stand-alone inertial sensor, a precision sensor (i.e. one that includes three axis accelerometers, gyroscopes and magnetometers) is preferably used.

There are some advantages in using multiple inertial sensors, particularly one mounted at the base of the spine and one just above the shoulder blades as shown in FIG. 1. Multiple sensors that are interconnected can be used to null some common mode errors are can be used to more accurately calculate the relative dynamic motion of the body trunk located between the sensors.

There are advantages to combining inertial sensors (or multiple inertial sensors) with a force plate as shown in FIG. 1, because a more accurate measurement of COG can be performed. Balance and specifically the limits of balance during dynamic activities (and especially large postural changes) will result in a significant mismatch between COG and COP. Trunk and or limb dynamic movement can be directly measured with an inertial sensor and used together with force plate data to obtain an accurate estimation of body orientation and dynamic motion.

In other embodiments, one or more three dimensional (3D) camera sensors 44 and 45 may be used to obtain information regarding the orientation of the subject 15 while standing or performing predetermined motions as described further below. Various methods are known in the art for optical 3D mapping, i.e., generating a 3D profile of the surface of an object by processing an optical image of the object. Some methods are based on projecting a speckle pattern onto the object, and then analyzing an image of the pattern on the object (for example U.S. Pat. No. 7,433,024). These systems reconstruct a 3D map of user. The term "3D map" refers to a set of 3D coordinates representing the surface of a given object, in this case the user's body. In other designs, the 3D camera device projects a pattern of spots onto the object and captures an image of the projected pattern, and then computes the 3D coordinates of points on the surface of the user's body by triangulation, based on transverse shifts of the spots in the pattern. Methods and devices for this sort of triangulation-based 3D mapping using a projected pattern are described, for example, in PCT International Publications WO 2007/043036, WO 2007/105205 and WO 2008/120217, whose disclosures are incorporated herein by reference. Alternatively, 3D cameras may use other methods of 3D mapping, using single or multiple cameras or other types of sensors, as are known in the art. By way of example, the Microsoft Kinect exemplary system provides a low cost 3D camera sensor.

The 3D camera sensor 44, the vibrotactile feedback mechanism 16, and the optional inertial sensors 12 and 13 may communicate with the intelligent controller 20 via conventional wired or wireless connections. For example, 3D camera sensor 44 may communicate directly to the intelligent controller 20 using a wired connection, such as a conventional universal serial bus (USB) connection or the like.

The 3D camera sensor (44 or 45) provides an instrument for measuring body sway as well as the biomechanical features such as, joint positions and angles of the subject 15 who is standing within the field of view of one or more 3D camera sensors. Specifically the 3D camera sensor provides a 3D map or image field to the intelligent controller. Image processing software on the intelligent controller processes the data, identifying the subject 15 in the image data field, identifying body segments (such as the torso or limbs) and tracking their position and orientations. Each segment can have combinations of translational and rotational degrees of freedom (DOFs) relative to a parent segment. The system automatically constructs the geometric postural skeleton structure, DOF relations, and DOF constraints between segments according to biomechanical principles that are well known in prior art. Each segment can be weighted and used in a skeletal model to calculate the body center of gravity (COG) location (as for example, described in V. Zatsiorsky "Kinetics of Human Motion" Section 4.3, Human Kinetics, 2002). Further, it may also be advantageous to calculate anterior-posterior (AP) and medio-lateral (ML) components of the COG and trunk sway angles from the postural segment data and display this in real time on a visual display. The center of gravity (COG) and trunk sway data for the subject can be readily calculated, in real time, by the intelligent controller. The data processing rate is usually restricted by the framing rate of the 3D camera sensor (for example 30 frames per second) however this is fast enough for real time motional therapy analysis.

Similarly, biomechanical features such as the trunk angle and position can be measured and the dynamic movement strategies of the subject can be estimated by the intelligent controller 20. For example, it is well known in prior art that static stance movement strategies may use ankle torque (or ankle strategy) or hip flexure (hip strategy) or a combination of the two during balance. Therefore, if the body segments are known at each frame instant (and the feet positions are fixed), the balance strategy can be identified from the trunk sway angle and relative angles between the ankle to hip (lower body segment) segment and hip to upper body (trunk) angle. If the upper and lower body segments move in the same direction or in phase with one another, then ankle strategy is being used and the human stance can be modeled as an inverted pendulum. Since the amount of force that can be generated by the muscles surrounding the ankle joint is relatively small, this strategy is generally used to control standing sway through a very small range of motion. In contrast to the ankle strategy, the hip strategy involves activation of the larger hip muscles and is used when the center of gravity must be moved more quickly back over the base of support as the speed or distance of sway increases. When using the hip strategy, the upper body (trunk) moves in a direction opposite to that of the lower body. Subjects may interchange between these postural control strategies (for example after instruction, environment). However, if the center of gravity is displaced beyond a maximum limit, or the speed of sway is so fast that the hip strategy is insufficient to maintain stability, then stability can only be maintained by finding a new base of support, for example by stepping. The 3D camera sensor 44 is advantageous as the complete motion and postural strategy employed by the subject 15 can be automatically determined by the intelligent controller 20, and displayed to the therapist 40.

In other embodiments, multiple 3D camera sensors 44, 45 can be used to increase the operation range or measurement capabilities of the motional training system 10. For example, 3D camera sensors 44 and 45 can be located on stands 43, to be off axis, but predominantly facing the subject 15. Multiple 3D camera sensors 44 and 45 should preferably be located orthogonally, approximately 2 m from the subject 15, thereby utilizing the full usable measurement range of the sensors and providing an accurate measurement of the anterior-posterior (front backwards) as well as medio-lateral (side to side) movement of the subject 15.

In general, the motional training system includes one or more sensors that measure appropriate subject body orientation and approximate the location of the center of gravity (COG). In certain cases, is possible to select other biomechanical features from the sensor information. For example, trunk sway angle may be readily used in place of COG provided that the degrees of freedom for the biomechanical system are limited (as would be the case for upright stance without hip flexure). As described in detail below, sensor information is used together with knowledge of various functional activities to predict and compare the actual body response and posture during various stages of each particular functional task.

The selection of sensors may depend on whether the system is a clinical system or a more portable take-home system. In the clinical environment, a force plate, multiple force plate sensors, or combinations of sensors are feasible. In other environments, cost and configuration simplicity may be the predominant factors in the determination of the mobility training system 10 sensor configuration. For example, home systems may preferably only include low cost force plate or 3D camera sensor embodiments.

Referring still to FIG. 1, the vibrotactile feedback mechanism 16 mounted on the subject 15 may include an arrangement of vibrotactile actuators as well as a controller and battery. Suitable vibrotactile actuators include, for example, the C-2 tactor and EMR actuators available from Engineering Acoustics Inc. (Casselberry, Fla.). The actuators are designed to be wearable on the body and may produce a strong displacement, i.e., vibration, within the frequency range of approximately 30 Hz to approximately 300 Hz. As such, the vibrotactile feedback mechanism 16 uses the sense of touch, i.e., the tactile sensory channel, as a technique for conveying information to the subject 15.

The sense of touch is processed via the somatosensory (SI) cortex in the brain. Various cutaneous sensory regions are mapped to different areas of the SI cortex, making the sense of touch both intuitive and implicitly linked to motion. In other words, the sense of touch is intrinsically linked with the neuro-motor channel, both at the reflex and higher cognitive regions, and is thus uniquely tied to orientation and localization.

Accordingly, the actuators of the vibrotactile feedback mechanism 16 are arranged and coupled to the subject 15, so that the actuators provide body-referenced, spatial information to the subject 15. Any number of actuators may be utilized. In particular, a direction or motion is mapped to a specific vibrotactile actuator, so that activation of the specific vibrotactile actuator and its associated location provide information with respect to that particular direction or motion. Motion may be also conveyed with a vibrotactile feedback mechanism 16 by the sequential and timed activation of a series of vibrotactile actuators, two or more actuators being spatially oriented with respect to the subject, so that the associated location and movement of vibrotactile stimulus provide information with respect to that particular rate and movement direction.

It has been demonstrated that tactile cueing is significantly faster and more accurate than comparable spatial auditory cues and is stable across a variety of body orientations, even when spatial translation is required. The vibrotactile feedback mechanism 16 is therefore an intuitive, non-intrusive feedback mechanism that may be more preferable to visual and audio cueing. In addition, temporal information can also be conveyed through the actuators in the vibrotactile feedback mechanism 16.

The intelligent controller 20 can be operated to drive the vibrotactile feedback mechanism 16 to provide feedback to the subject 15 during motional training. This feedback may include spatially oriented and body-referenced information, temporal information, information based on sequences or patterns of pulses, as well as information based on vibration frequency. As described previously, the spatially oriented and body-referenced information may include directional information based on the location of the vibrotactile stimulus. The temporal information may be provided according to pulse timing, where more rapid pulses indicate a greater urgency. Information based on vibration frequency may be provided according to high and low frequencies which can be discerned by the subject 15, where frequencies of approximately 250 Hz may, for example, indicate a greater urgency and frequencies less than 120 Hz may indicate less urgency.

The therapist 40 may interface with the intelligent controller 20 and associated motional training system 10 system software via the screen display 30 and the keyboard 31. However, to make it easier for the therapist 40 to monitor and assist the subject 15 during the motional training, the therapist 40 may alternatively use the remote interface 41 to control aspects of the motional training system 10 as described further below.

In addition, because the vibrotactile feedback mechanism 16 provides information directly to the subject 15 undergoing motional training, the motional training system 10 may provide the therapist 40 with a similar vibrotactile feedback mechanism 42 as shown in FIG. 1. such that the therapist 40 can monitor the information that the subject 15 is receiving.

Figure 2:
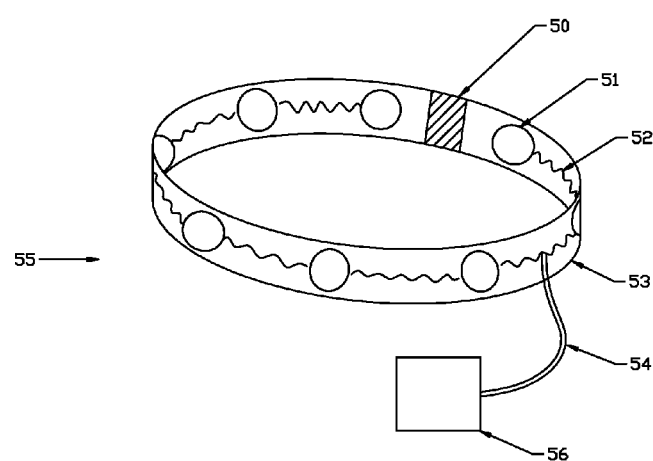
FIG. 2 illustrates an embodiment of a vibrotactile belt according to aspects of the present invention.

An embodiment of a vibrotactile feedback mechanism 16 is illustrated in FIG. 2 as a vibrotactile belt 55. The vibrotactile belt 55 may be worn around the torso by the subject 15 as shown in FIG. 1. The vibrotactile belt 55 includes a plurality of actuators 51 that are spaced equally around a band 53. As described previously, in one embodiment, the vibrotactile belt 55 employs an array of eight C-2 tactors available from Engineering Acoustics Inc. (Casselberry, Fla.). For example, eight actuators may be employed so that when the subject 15 wears the belt, one actuator 51 is centered on the front of the subject 15, e.g., aligned with the belly button. Correspondingly, another actuator 51 is aligned with the spine, another actuator 51 is aligned with the right side of the torso, and another actuator 51 is aligned with the left side of the torso. When the actuators 51 are oriented in this manner, each of the eight actuators 51 may represent a direction relative to the subject 15 similar to the eight major points on a compass, i.e., east, west, north, northeast, northwest, south, southeast, and southwest. Other embodiments may include an array with more or less tactors.

The vibrotactile belt 55, for example, may be formed with a band 53 of stretch fabric with a fastener 50, which may include a hook-and-loop fastener, button, zipper, clip, or the like. A wire 52 extends between each pair of actuators 51 and is of sufficient of length to allow the band 53 to stretch when worn by the subject 15. In particular, the wire 52 may be looped or coiled and mounted to the belt 55. The actuators 51 are connected to control electronics 56 via a wire harness 54. The control electronics 56 may include a microcontroller with analog to digital converters, circuitry for interfacing with sensors, digital-to-analog converters, and a series of amplifiers. The actuators 51 are optimized for exciting the tactile response by at the skin. In some embodiments, the actuators 51 are linear actuators.

This vibrotactile belt 55 may also employ additional sensors, such as direction sensors (not shown), which operate with the control electronics 56 and interface with the system intelligent controller 20, for example via the wireless data connection 21. Additional directional sensors may be used to determine the orientation of the subject 15 with respect to the force plates 11a and 11b to be used by the intelligent controller in motional tasks described hereinafter for the determination of vibrotactile feedback 16. Further, additional directional sensors may be used to determine the orientation of the subject with respect to the therapist 40 and to allow the vibrotactile feedback mechanism 42 on the therapist 40 to indicate the position of the vibrotactile feedback mechanism 16 on the subject. The position of the vibrotactile feedback mechanism 16 may be indicated to the therapist 40 in a format that is independent of or dependent on the orientation of the therapist 40.

Figure 3:
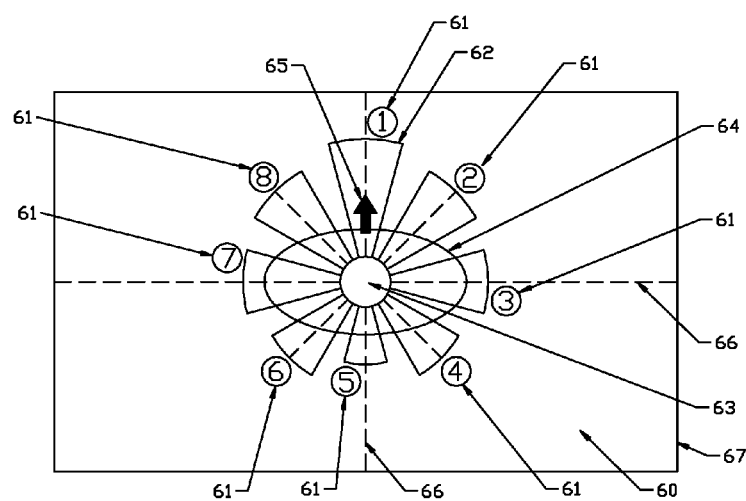
FIG. 3 illustrates an example of vibrotactile feedback that may be employed according to aspects of the present invention.

FIG. 3 illustrates a screen display 67 that may be shown by the intelligent controller 20 on the display monitor 30. The screen display 67 provides a view 60 that shows the center of pressure (COP) 63 of the subject 15 as determined via the force plates 11a and 11b or derived from combinational sensors. The view 60 also shows a training region that corresponds to an area in which the subject is expected to perform a predetermined motion as a part of motional training on the force plates 11a and 11b. Accordingly, the screen display 67 may be used to monitor activity by the subject 15 on the force plates 11a and 11b, and to provide visual feedback to complement the information provided by the vibrotactile feedback mechanism 16. In addition, the screen display 67 may be employed to set parameters or thresholds for operation of the vibrotactile feedback mechanism 16.

As FIG. 3 further illustrates, the view 60 also shows information relating to the vibrotactile feedback mechanism 16. In particular, the view 60 shows a series of eight segments, or zones, 61 around the perimeter of a representation 64 of the subject 15. The subject 15 is facing in a direction indicated by the arrow 65 in FIG. 3. Each segment 61 corresponds to an actuator 51 on the vibrotactile feedback mechanism 16. In the embodiment of FIG. 3, there are eight segments corresponding to eight actuators on the vibrotactile feedback mechanism 16. As described previously, the vibrotactile feedback mechanism 16 may be oriented so that one of the eight actuators 51 is centered on the front of the subject 15, another actuator 51 is aligned with the spine, another actuator 51 is aligned with the right side, and another actuator 51 is aligned with the left side. Therefore, the segment 160 shown in FIG. 3 may correspond with the actuator 51 on the front of the subject, the segment 164 may correspond with the actuator 51 aligned with the spine, and segments 162 and 166 correspond with the actuators 51 on the right and left sides, respectively. Each segment 61 includes an arc 62 that represents an adjustable threshold for each corresponding vibrotactile actuator 51. In other words, the width of the arc 62 as well as the length of the segment 61 may be configured to set thresholds that determine when the actuators 51 are activated to provide feedback. If, for example, the COP 63 of the subject 15 moves to a region beyond a segment 61 and arc 62, the corresponding vibrotactile actuator 51 may be activated. In other words, when there is a variance between the determined location of the COP 63, a vibrotactile actuator is activated. Similarly, in another example a vibrotactile actuator 51 may be activated until the COP 63 of the subject 15 moves to a corresponding region beyond a segment 61 and arc 62. Thus, the segments 61 and arc 62 may correspond to thresholds that define the boundaries for movement by the subject 15. The thresholds are selected so that information regarding movement of the subject relative to these thresholds provides useful information during motional therapy.

It is noted that movement of the COP 63 can be caused when the subject sways, and movement by foot or other significant movement is not required. As such, the example embodiment illustrated by FIG. 2 can assess static balance.

During an example operation of the motional training system 10, the subject 15 attempts to move according to one or more motions defined as a part of the motional training, e.g., moving from a sitting position to a standing position to test static balance. These predetermined motions may make up all or part of a functional activity. The force plates 11a and 11b react to the attempt by the subject 15 to move according to the predetermined motions. In particular, the force plates 11a and 11b determine corresponding movement of the COP 63 and communicate this information to the intelligent controller 20. As discussed previously, thresholds may be visually defined on the display monitor 30 via the intelligent controller 20 in terms of segments 61 and arcs 62. In one embodiment, if the intelligent controller 20 determines that the COP 63 has moved beyond any of the segments 61 and past any of arcs 62, the intelligent controller 20 activates the actuator 51 corresponding to the segment 61. Thus, the subject 15 receives a vibrotactile stimulus, or feedback, when there is a variance between the location of the COP 63 and the segments 61 and the arcs 62.

Before operation, the COP 63 is initially zeroed, or reset, to align the axes 66 and the segments 61 over the COP 63. However, the axes 66 may also be zeroed after a subset of the predetermined motions during the motional therapy. The therapist 40 may zero the axes 66 and segments 61, for example, via the therapist remote interface 41 while monitoring the subject's attempt to perform a set of predetermined motions. The motional training system 10 allows the subject 15 to sequentially move from one region to another according to the set of predetermined motions, e.g. from a sitting position to a standing position and so on. Zeroing allows to each region, i.e., a subset of the predetermined motions. Otherwise, the thresholds would only apply to the set of predetermined motions as a whole.

Figure 4:
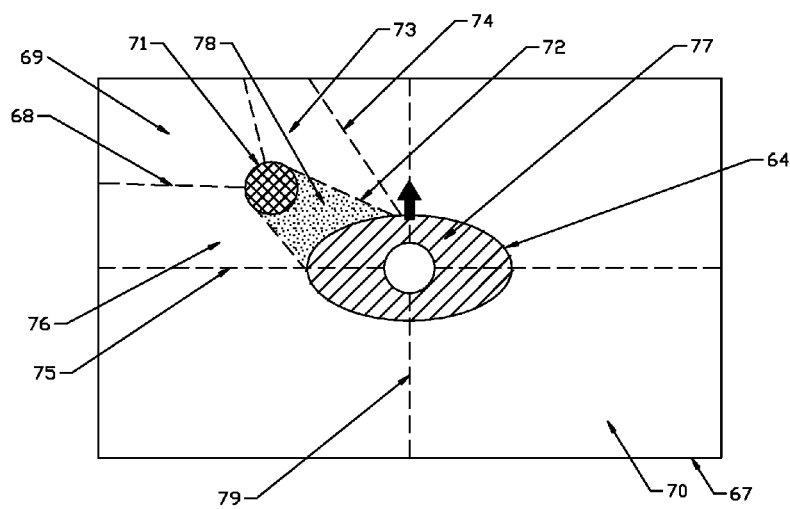
FIG. 4 illustrates another example of vibrotactile feedback that may be employed according to aspects of the present invention.

FIG. 4 illustrates another view 70 that may be provided on the screen display 67. The view 70 is also a top view that shows a representation 64 of the subject 15, a COP 77 of the subject 15, a target area 71, and navigation limits 72. The COP 77 is initially zeroed or reset to locate the axes 75 and 79 over the COP 77.

The predetermined motions corresponding to a functional activity may require the subject 15, and thus the COP 77, to move from one area to another. Accordingly, in some embodiments, vibrotactile cueing may be employed to guide the subject 15 to the specific target area 71. In particular, using the motional training system 10, the subject 15 is encouraged via vibrotactile cueing to move his COP 77 until it reaches the target zone area 71. Vibrotactile cueing may initially activate the actuator 51 that corresponds to the segment facing the target 71. The activation of that actuator 51 causes the subject to turn toward the target area 71. Movement to the target area 71 may require the COP 77 to traverse an intermediate zone 78. Vibrotactile pulses may be modulated to indicate the range to the target area 71. For example, the vibrotactile feedback with a frequency of 250 Hz and duration of 300 ms may be pulsed initially at 0.1 Hz, pulsed at 1 Hz in the intermediate zone 78, and then pulsed at 5 Hz when the target area 71 is reached. Alternatively, vibrotactile pulses may be modulated to indicate the rate at which the COP 77 is approaching the target area 71. For example, the vibrotactile feedback with a frequency of 250 Hz and duration of 300 ms may be pulsed initially at 0.1 Hz, pulsed at between 1 Hz and 5 Hz based on the rate of COP 77 movement during movement in the intermediate zone 78, and then pulsed at 5 Hz when the target area 71 is reached.

Directional or navigation feedback may also be provided to the subject 15 using adjacent actuators 51. For example, if the COP 77 shown in the view 70 moves off target, i.e., out of the intermediate segment 78, into the adjacent segment 73 defined between segments 72 and 74, the corresponding actuator 51 associated with the segment 73 may be pulsed at a low frequency 15 Hz amplitude modulation to indicate that the subject is off target. Alternatively, directional feedback can be provided by activating the actuator 51 that corresponds to the segment 76, which is the segment on the opposite side of the intermediate segment 78. In this case, the vibrotactile cueing is provided as a "tether" and signals the subject 15 to move in the direction of the vibrotactile stimulation. As shown in the view 70, the representation 64 of the subject 15 positioned in the segment 73 would be drawn back to the segment 78 as the representation 64 moves toward the segment 76 in response to the activation of the actuator 51 corresponding to segment 76.

Further vibrotactile feedback can be communicated to the subject 15 to indicate to the subject is that the target area 71 has been reached. This vibrotactile feedback, for example, may include pulsing two front actuators 51 alternately, and then pulsing one back actuator 51. The subject 15 may learn the various messages associated with the vibrotactile feedback before the start of the motional training.

Once the target 71 has been reached, the therapist 40 may also elect to move the axes 79 and 76 to the new location 71 and revert to the view 60 as shown in FIG. 3. Alternatively, the therapist may elect to guide the subject to a new target. Indeed the new target may be the initial starting position.

As a further example of the usefulness of the systems and methods of the invention, embodiments thereof may be employed to treat stroke subjects with Pusher Syndrome. These subjects suffer from disturbed body orientation that drives both conscious perception of body orientation and abnormal muscle activation patterns or synergies. For example, subjects with Pusher Syndrome may perceive that their bodies are oriented in an upright position when in fact their bodies may be leaning by as much as 20 degrees towards the side of the brain lesion. When sitting or standing, the nonparetic extremities push lateral balance to the hemiparetic side. The phenomenon is present in approximately 79% of all acute strokes that resolves to 10% by 6 months (early intervention may eliminate Pusher Syndrome altogether), and is present in both left and right sided CVA. Subjects with Pusher Syndrome may have a normal perception of visual vertical, but they may be unable to perceive that their body posture may be leaning severely. Observations suggest that Pusher Syndrome affects the neurological pathway that is integral to sensing orientation of gravity and controlling upright body posture.

Treatment of subjects with Pusher Syndrome can be achieved by employing the vibrotactile feedback mechanism 16 to provide the subject a reference for body-orientation. If the subject shows a tendency to lean to a particular side, the length of the segment arc 62 corresponding to the opposite side is adjusted to be closer to the COP 63. The vibrotactile feedback mechanism 16 is set to activate the corresponding actuator 51 if the COP 63 moves over a particular segment arc 62. For example, if a subject leans to the right, segment 166 on the left side as shown in FIG. 3 is defined to provide a smaller threshold relative to the COP 63. In the normal maladapted stance, the subject feels vibrotactile feedback on the left side unless the subject leans further towards the right. The therapist can therefore use the invention to provide an additional sensory feedback reference which can be used for neurological retraining A similar effect can be achieved using the technique described with reference to FIG. 4. In this case, a target 71 is configured on the left hand side of the subject, e.g., on axis 75, and used as a goal for the subject to shift their weight from the initial maladapted state 77 towards postural correction. In each example, the therapy may be practiced and repeated over several sessions, including various other tasks to enrich and diversify the learning environment. The therapist 40 may also adapt the segment thresholds and target locations in each of the examples, based on the subject performance during this task.

FIGS. 5a, 5b, 5c and 5d depict an example of a sequence of predetermined motions that define a functional transitional movement task. The transition from a sitting position to a standing is an extremely important functional activity. FIGS. 5a, 5b, 5c and 5d illustrate the sub-tasks that make up this functional task. The motional kinematics for this particular functional task are described by Patrick D. Roberts and Gin McCollum (Dynamics of the sit-to-stand movement, Biological Cybernetics, Volume 74, Number 2/January, 1996). This reference shows that some of the sub-tasks may be conditionally stable or unstable. The embodiment provides a technique for guiding the subject 80 through the sequence of sub-tasks and providing feedback to the subject 80 to help the subject 80 complete the functional task. The embodiment further provides a technique for repetitively guiding the subject 80 through a sub-activity to help the subject 80 learn the sub-activity.

Figure 5A:
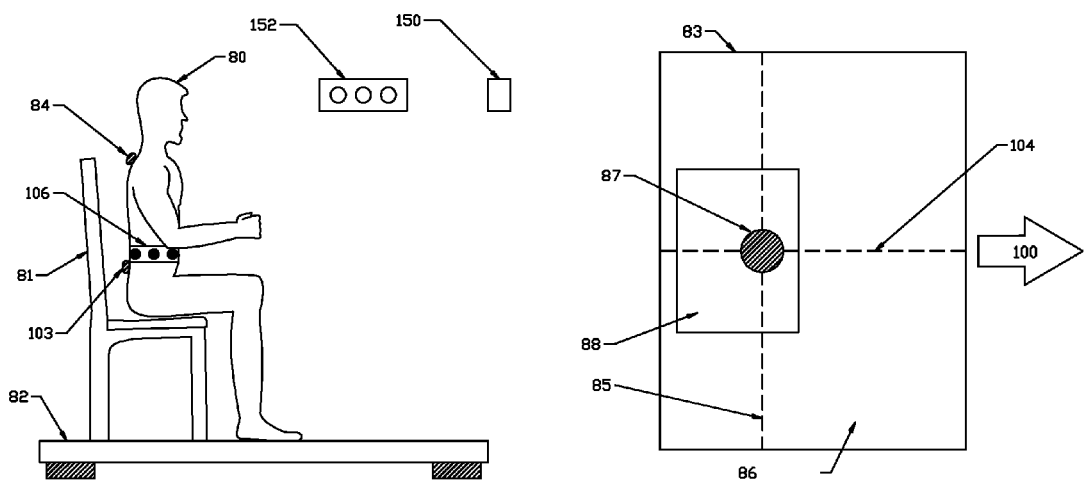
FIG. 5A illustrates a sub-task in a functional task that is the subject of motional training according to aspects of the present invention.

FIG. 5a shows a subject 80 initially at rest in a sitting position on a chair 81 disposed on a force plate 82. The subject wears a vibrotactile belt 106 around his torso. An inertial sensor 103 may be mounted at the lower back of the subject 80 and an inertial sensor 84 may be mounted at the upper shoulder of the subject 80 to provide additional information. Specifically, the spine angle, bend and other postural information from the inertial sensors 103 and 84 may be helpful in determining subject transitional motion characteristics.

In another embodiment, one or more 3D camera sensors 150 and 152, may be used for the measurement of the subjects 80 COG location and postural orientation during the activities described in further detail below. Preferably, at least one 3D camera sensor, for example 150, should be placed facing the front of subject 80, and at least one 3D camera, for example 152, should be placed to the side of subject 80. In another example, one or 3D cameras may be placed at an auxiliary view, facing the subject 80 at a point between the aforementioned front and side camera positions. One or more 3D camera sensors may be preferentially used in combination with one or more force plate sensors 82. In each case, the subject's postural signals and orientation is calculated from the COG (derived from the 3D camera sensor data) and estimated skeletal postural model (calculated on the intelligent controller 20), and can be used together with the force plate data (if available) to calculate an accurate depiction of the COP and further identify what particular movement stage, or sub-task the subject 80 may be completing.

FIG. 5a also shows a corresponding top view 83 of the force plate area. The view 83 may also be shown as a screen display on the display monitor 30, and may be used by the therapist 40 to monitor activity and/or configure a training region. In addition, the view 83 may provide visual feedback that complements the vibrotactile feedback received by the subject 80. The subject is orientated to face in the direction shown by arrow 100. The chair takes up an area 88. While seated, the subject COP 87 is located within the chair area 88. System axes 104 and 85 are initially defined to coincide with a static stable seating. It should be noted that the COP data and vibrotactile belt 106 can easily be used to provide the subject 80 with postural feedback while seated. If the COP 87 moves outside a predefined segment, i.e., a variance occurs, the corresponding body referenced tactile transducer can be used to alert the subject 80 to correct his or her posture. In this case, the limits of the segment need to be close to the axes 85 and 104 as the excursion of a subject's COP 87 during sitting is relatively small.

Figure 5B:
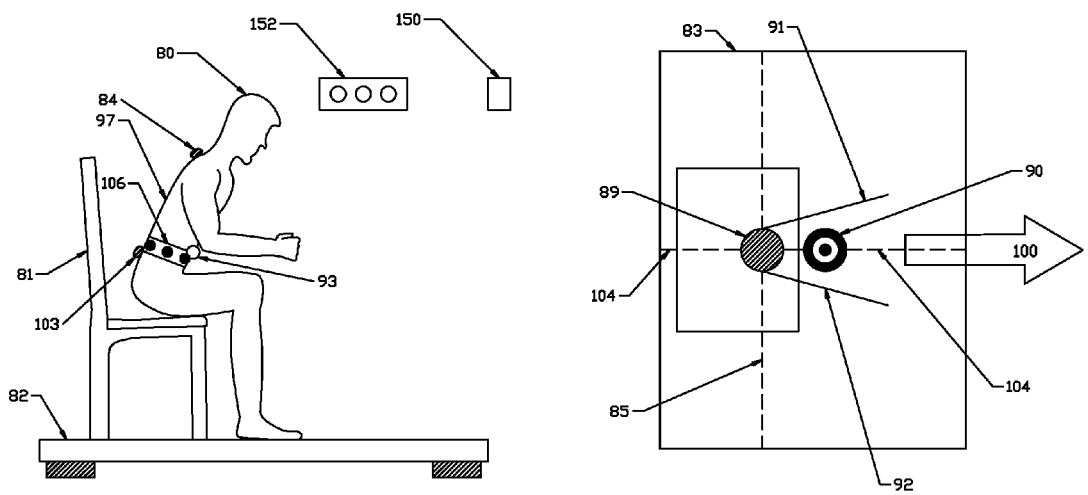
FIG. 5B illustrates another sub-task in the functional task of FIG. 5A.

FIG. 5b shows the next sub-task in the sequence. In particular, the subject 80 moves from the sitting position on a chair 81 to an upper body forward lean position 97. The subject 80 is guided into the lean position 97 by the intelligent controller 20 based on measurement of the patient 80 COP 87 and sensor information. In particular, the intelligent controller 20 may provide vibrotactile cueing by activating the actuator of positioned at the front of the subject 80.

FIG. 5b shows a corresponding top view 83 of the force plate area. The subject 80 is orientated to face in the direction shown by arrow 100. The COP 89 of the subject 80 is shown with axes 85 and 104. It is desirable to guide or cue the subject 80 to move his COP 89 onto a target area 90. During the process of translating the COP 89 towards the target area 90, it is also desirable that the COP 89 stay within moving bounds 91 and 92. If the COP moves outside the bounds 91, vibrotactile feedback is then applied to the subject to correct the translation. The target region 90 may be set to shapes other than a circle, such as a rectangle, and may be positioned off the axis 104 to counter any subject asymmetrical tendencies.

Figure 5C:
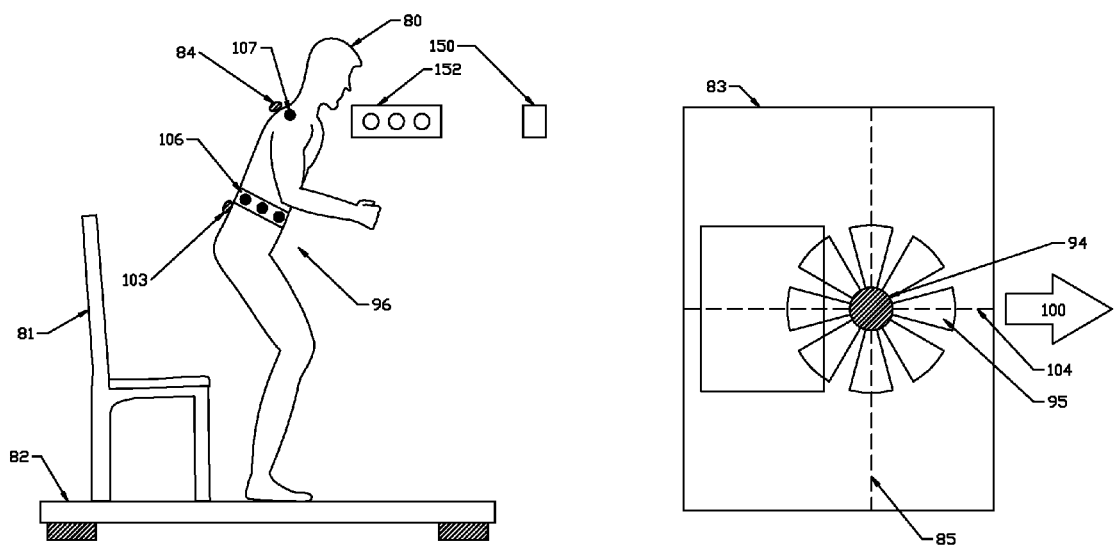
FIG. 5C illustrates a further sub-task in the functional task of FIG. 5A.

FIG. 5c shows the next further sub-task in the sequence. In particular, the subject 80 transitions to an initial stance 96 after moving from a sitting position on the chair 81. An additional vibrotactile feedback mechanism 107 may be mounted on the subject's upper body. Lean is no longer encouraged and the subject 80 is guided to a stable balance by the intelligent controller 20 by providing vibrotactile cueing. The subject 80 is also guided to regain upright posture. The sensors 84 and 103 may be used to determine the spine trunk lean angle and provide this information to the intelligent controller 20. The controller 20 then provides vibrotactile feedback 106, preferably via a pattern of vibrotactile signals representing a message. Alternately an additional vibrotactile feedback 107 can be used to provide directional cueing i.e. a vibrotactile stimulus on the neck, shoulders or upper body to guide the subject 80 to move towards the stimulus and regain upright stance. A tactile message is thus a reminder to the subject 80 and eliminates the need for a verbal instruction.

FIG. 5c shows a view 83 of the force plate area. The subject is orientated to face in the direction shown by arrow 100. The COP 94 is aligned with axes 104 and 85. When compared to the initial position of the axes shown in FIG. 5a, these axes have shifted in the direction of the arrow 100. Vibrotactile feedback can be applied to the subject 80 according to the technique described with reference to FIG. 3. Various segments 95 represent areas beyond which a body referenced vibrotactile signal is applied to indicate to the subject that the threshold has been exceeded in a particular zone, i.e., a variance has been created.

Figure 5D:
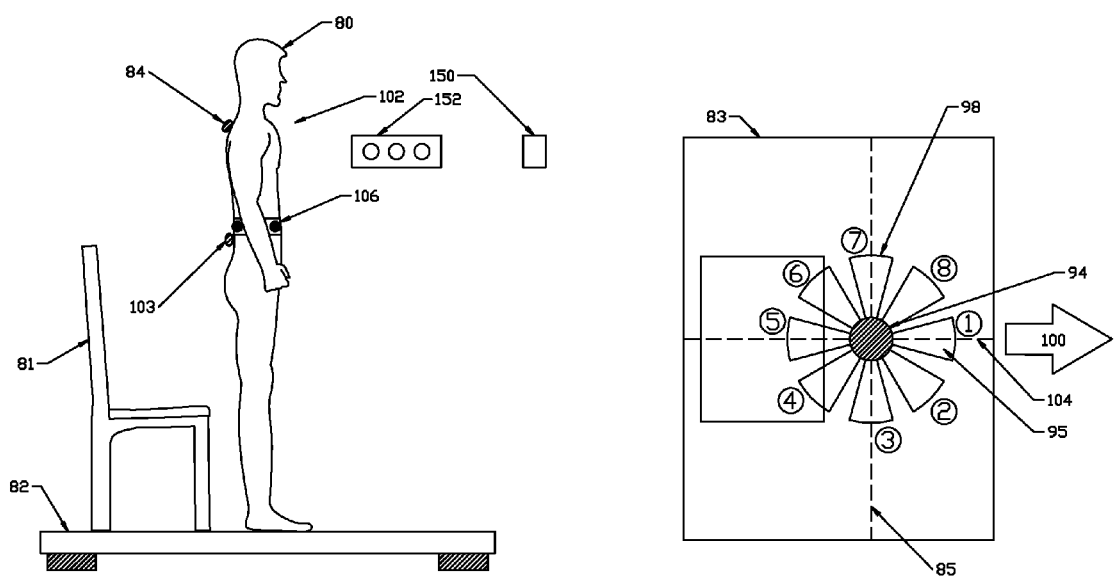
FIG. 5D illustrates yet another sub-task in the functional task of FIG. 5A.

FIG. 5d shows the subject 80 who has attained an upright stance 102. The forward lean no longer exists and the subject 80 is now assisted in quiet stance. The intelligent controller 20 provides vibrotactile cueing 98 when the COP 94 moves beyond the defined thresholds. The inertial sensors 84 and 103 may be employed to confirm spine angle. The inertial sensor 84 may also provide heading (or trajectory) information to the intelligent controller 20 and provide corrective feedback if the subject is not facing in the direction of the arrow 100.

FIG. 5d also shows a corresponding view 83 of the force plate area. The subject faces in the direction shown by arrow 100. The axes 85 and 104 coincide with the initial location of the COP 94. Similar to view 60 of FIG. 3, the view 83 shows a series of segments 95 that indicate the thresholds for movement of the COP 94 and determine when the appropriate vibrotactile actuator is activated.

Figure 5E:
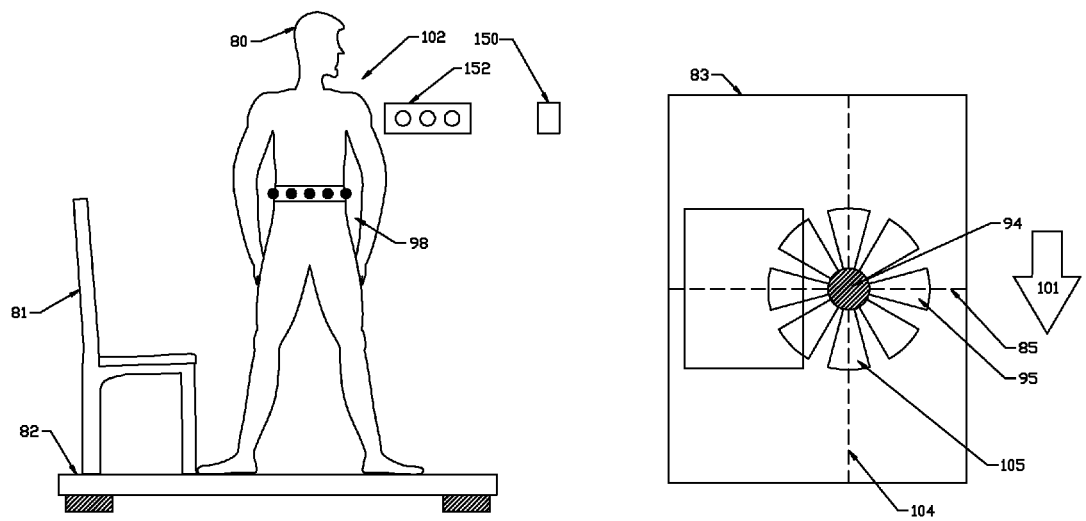
FIG. 5E illustrates a further sub-task in a sit-to-stand functional task.

FIG. 5e illustrates another sub-task in the sit-to stand functional task. After completing the sub-tasks described previously, the subject 80 now performs a full body turn to the right and resumes a stable stance. The subject 80 is guided through a turn to the right through vibrotactile cueing. In particular, one or more actuators on the right side of the subject 80 are activated to initiate a turn to the right. The inertial sensor 103 may provide heading data to the intelligent controller 20.

FIG. 5e also shows the corresponding view 83 of the force plate area. The subject faces in the direction shown by arrow 101. The vibrotactile belt 98 is orientated in the direction that the subject is facing, so that the front segment now corresponds with the segment 105 shown in the view 84. Similar to the view 60 of FIG. 3, the view 83 shows a series of segments 95 that also indicate the thresholds for movement of the COP 94 and determine when the appropriate vibrotactile actuator is activated.

In an alternate embodiment, the top view 83 may depict an activity area and the measured kinematic variable may be the subject's COG calculated using one or more 3D camera sensors. The COG may be displayed on a 2D display in the same way as COP (as described hereinbefore), or alternately, on a 3D display where the actual trajectory of the subject's COG may be displayed in real time.

Figure 6A:
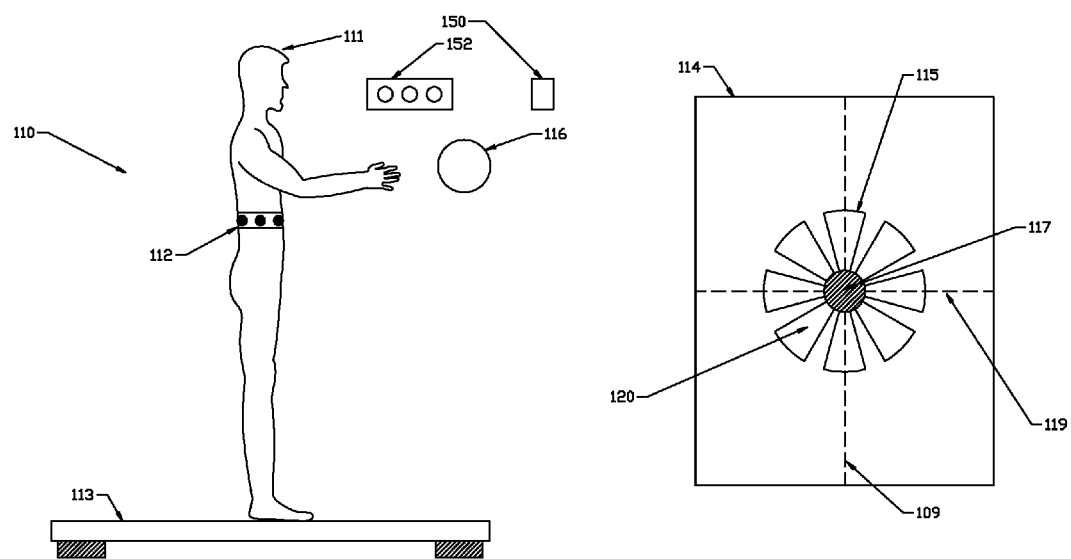
FIG. 6A illustrates a sub-task in a functional task that is the subject of motional training according to aspects of the present invention.

Referring now to FIG. 6a, an example of a functional task 110 is illustrated where a subject 111 stands on a force plate 113 and reaches for a target object 116. The vibrotactile belt 112 provides feedback to guide the subject 111 through the task 111. The corresponding top view 114 also shown in FIG. 6a is similar to the view 60 of FIG. 3. The view 114 shows a series of segments 120 that indicate the thresholds for movement of the COP 120 and determine when the appropriate vibrotactile actuator is activated. Alternatively, the view 114 may be employed to provide vibrotactile cueing which guides the subject 111 through the necessary sub-task movements with the vibrotactile belt 112.

Figure 6B:
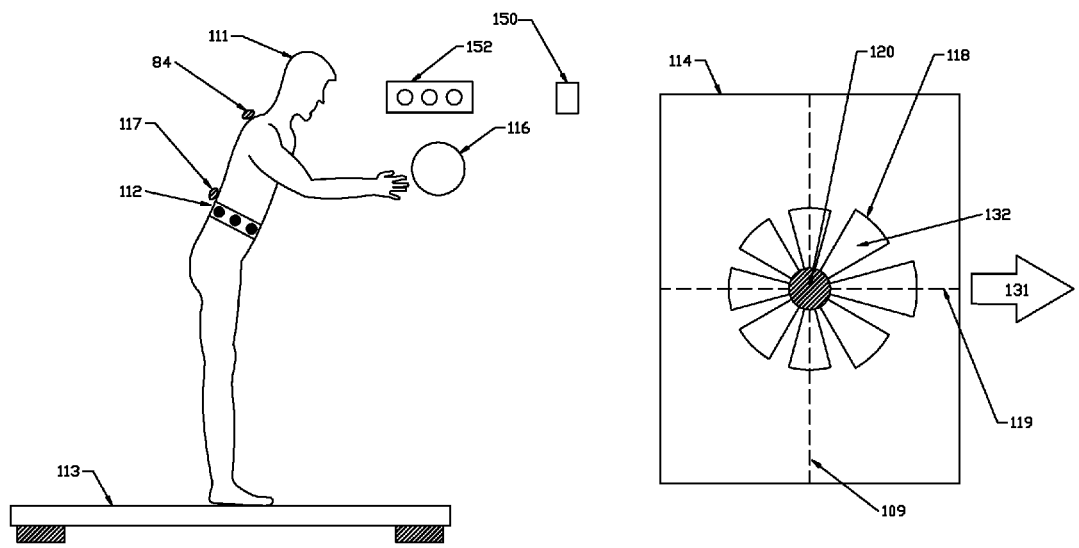
FIG. 6B illustrates another sub-task in the functional task of FIG. 5A.

FIG. 6b illustrates the subject 111 reaching for the target object 116 while standing on a force plate 113. Inertial sensors 117 and 130 may provide additional information about bend angle and posture. An intelligent controller 20 uses the force plate 113 and sensor information to provide sub-task specific vibrotactile feedback to the subject 111 with the vibrotactile belt 112.

FIG. 6b also shows the corresponding top view 114 with the subject 111 facing in direction 131. Similar to the view 60 of FIG. 3, a series of segments 132 indicate the thresholds for movement of the COP 120 and determine when the appropriate vibrotactile actuator is activated.

Figure 7:
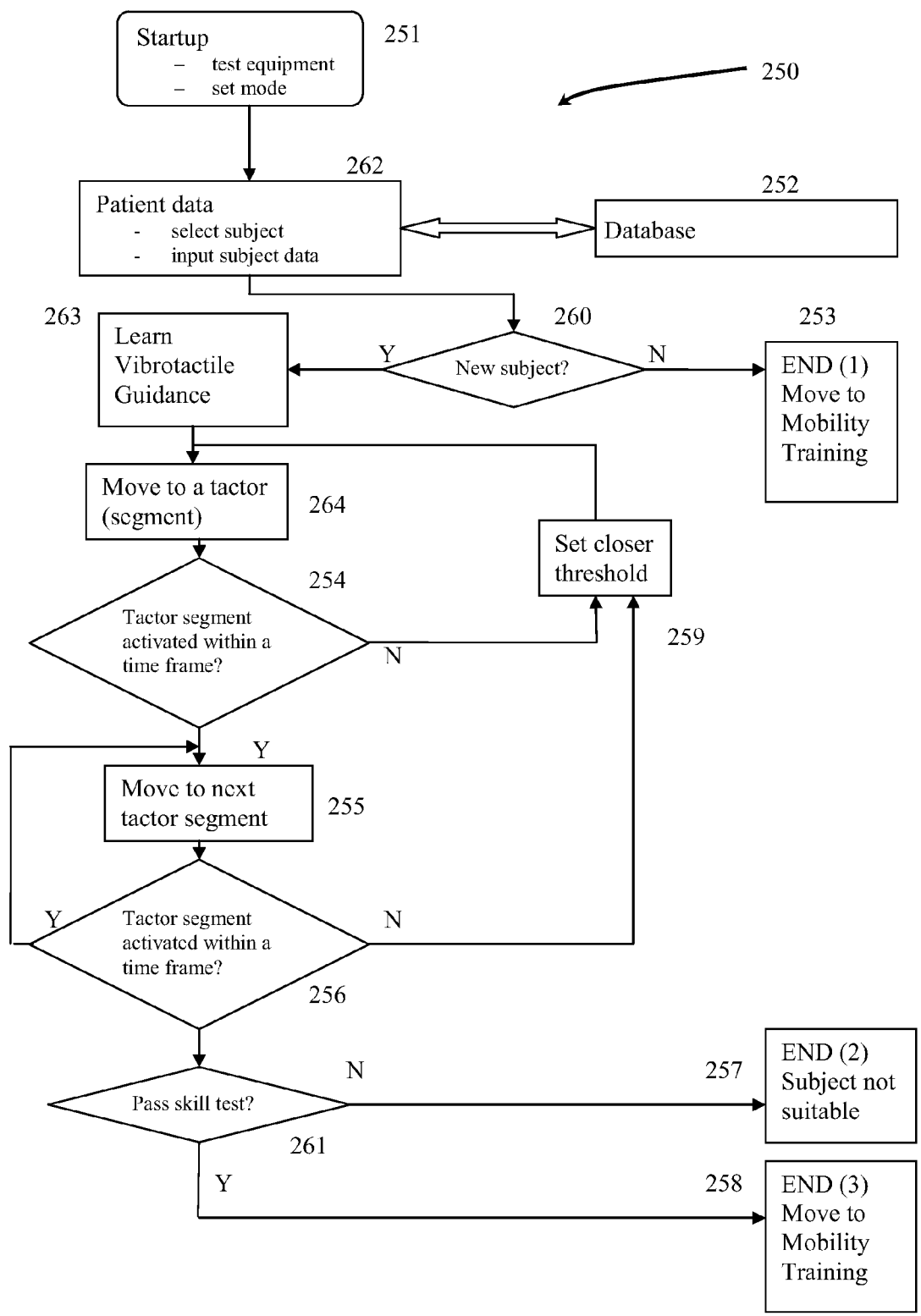
FIG. 7A illustrates program flow and system logic for motional training according to aspects of the present invention.
FIG. 7B illustrates another program flow and system logic for motional training according to aspects of the present invention.
FIG. 7C illustrates further program flow and system logic for the motional training according to aspects of the present invention
Figure 7:
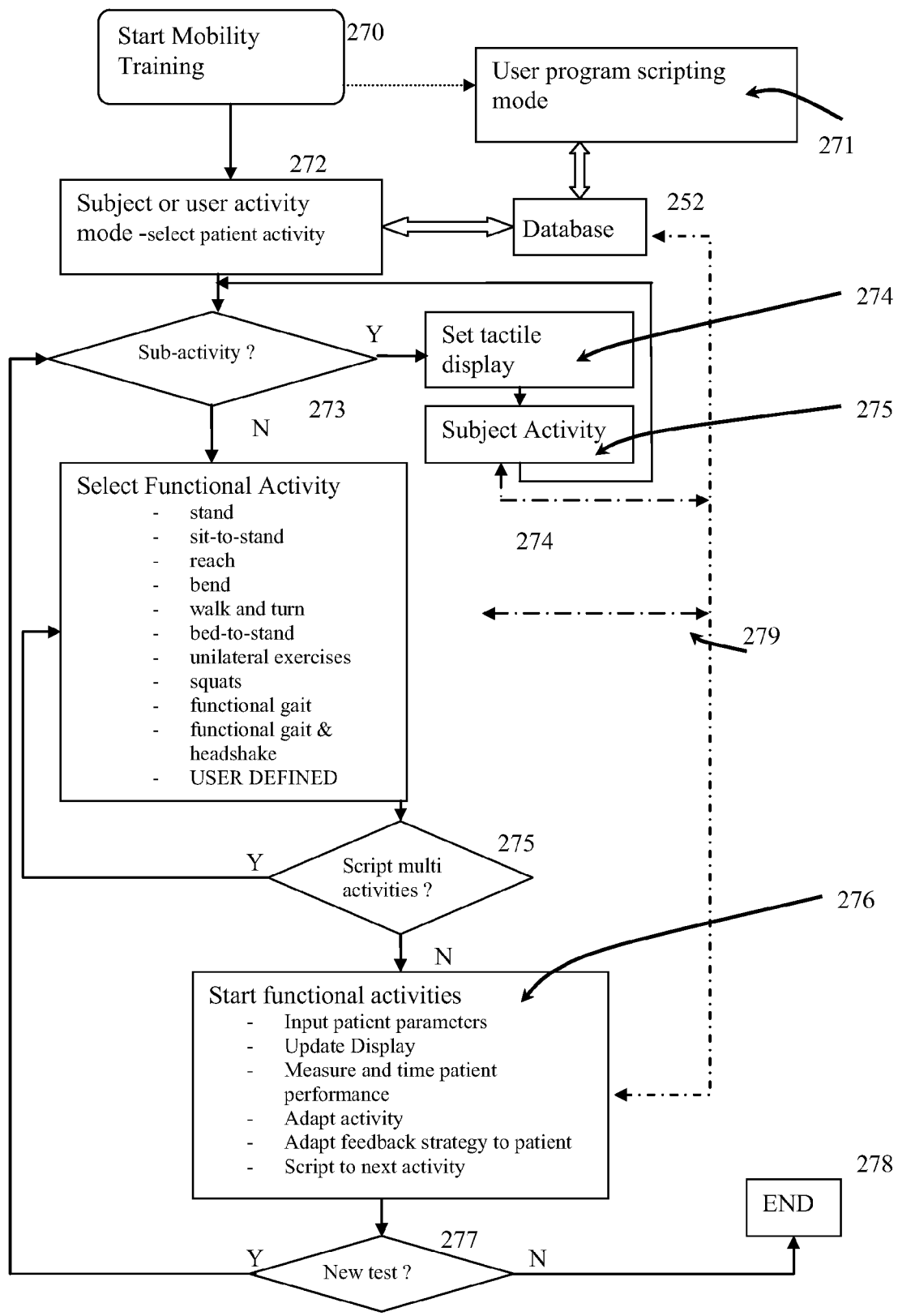
Figure 7:
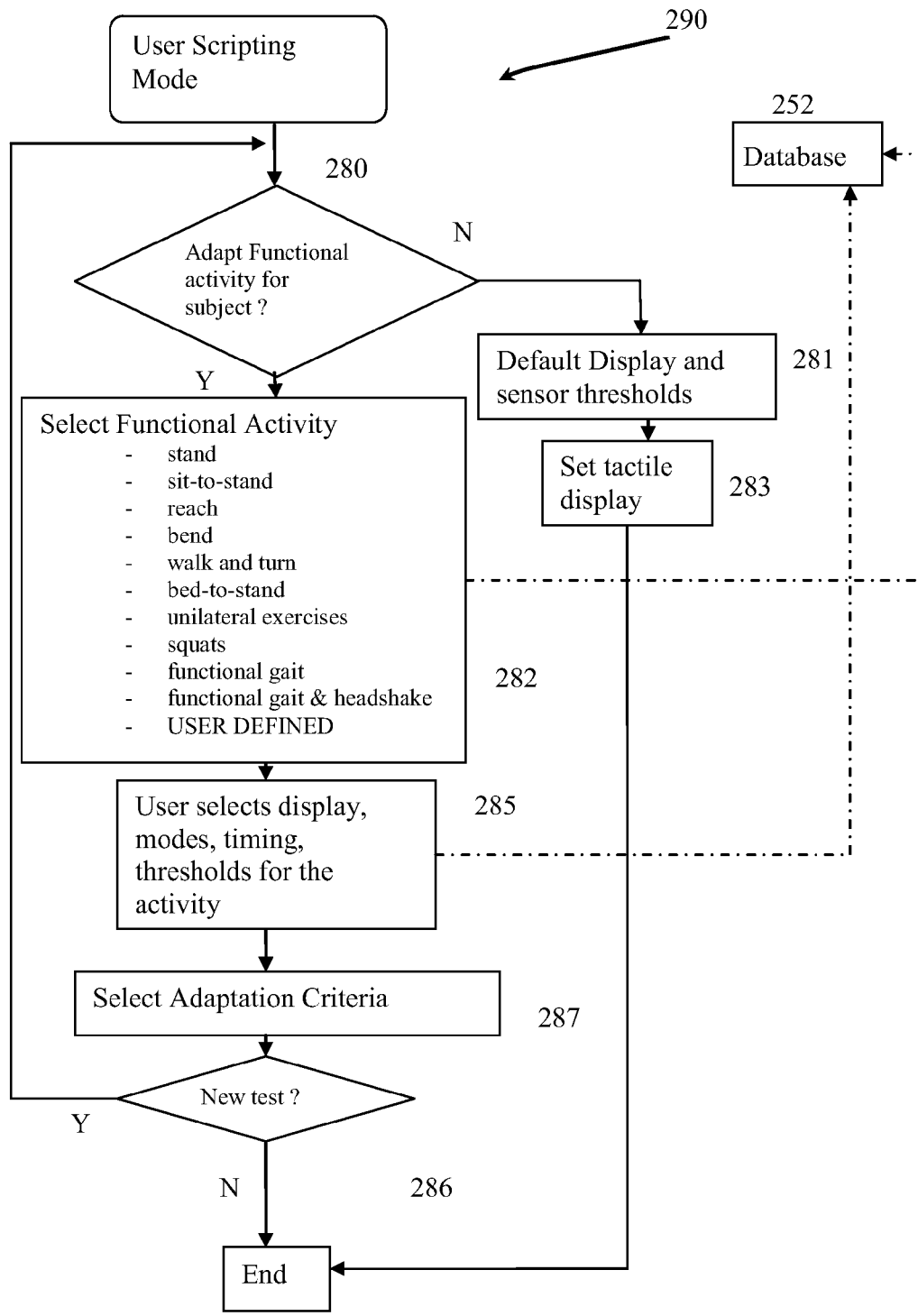

FIGS. 7a, 7b, and 7c show an example program flow and example system logic for the motional training system 10. The program flow includes three main routines; a test shown in FIG. 7a for new subjects to determine whether they will be suitable candidates for vibrotactile guided training, a scripting routine, and configuration tool for therapists trainers to design their own functional movement tasks as shown in FIG. 7c and a series of functional movement tasks as shown in FIG. 7b. The functional tasks 274 include tasks and sub-tasks, sensor measurements, processing, visual and vibrotactile feedback data, adaptive changes to the tasks and feedback parameters, database storage, and retrieval of information. A feature in the operation of the program and system is the ability to adapt the task for the subject and also adapt the vibrotactile thresholds and feedback. These adaptations are completed automatically by the system using an assessment of the subject performance in the task.

FIG. 7a illustrates the example program control logic for a test 250 and a start-up step 251 for the determination of subject or user suitability for vibrotactile guided motional training. Subject data is either selected or entered at step 262. A database 252 is employed to store, retrieve and collect subject information as well as specific components and data related to vibrotactile guided motional training activities. New subjects undergo initial training at step 263, e.g., the subject is shown, typically but not necessary by a therapist, how the vibrotactile actuators activated during movement by the subject. In particular, the segment thresholds as described previously are set to cause activation of particular actuators when the subject moves his COP in a corresponding direction for defined distances or thresholds as described hereinbefore. The subject is instructed, for example, to lean to the side and activate a corresponding vibrotactile actuator in step 264. If the subject fails to comply or is unable to reach the threshold to activate the particular actuator within a time threshold 254, e.g., approximately about 5 seconds, the system may alert the therapist and move the threshold for activation closer to the COP. The time threshold may be normalized for subject age and ability. If the subject is able to activate the particular actuator, however, the subject is then instructed to move and activate another actuator in step 255. Each subsequent activation of a particular vibrotactile actuator should also be activated within a similar time threshold 256, to that set during the initial movement test 254. If the subject fails to activate 50% of the actuators, for example, at a default threshold 261, the system may determine in step 257 that the subject is not suitable for vibrotactile guided training. Subjects who are able to show sufficient competence may move onto other functional tasks in step 258.

FIG. 7b shows an example program control logic for vibrotactile guided motional training 270. In this example the therapist may employ two modes: a program scripting mode 271 and a subject activity mode 272. The program scripting mode 271 allows the therapist to configure and program new functional tasks that are stored in a system database 252. The subject activity mode 272 may use this database 252. Vibrotactile guided motional training may include states that contain sub-tasks 273, which may be defined according to the types of vibrotactile feedback techniques described with reference to FIG. 3 or 4. The particular vibrotactile feedback mode and sub-task 273 may be chosen by the therapist for subject task activity 275. Sub-task vibrotactile guided training is completed to ensure that the subject masters and practices the necessary mobility skills for functional tasks. The definitions of the functional tasks and sub-tasks, together with subject data, and user defined parameters are stored in a system database 252 and may be accessed 279 for the selection of a functional task 274. The system also permits multiple tasks 275 to be concatenated to create more complex functional task sequences. Once the task 274 and task combination have been selected, the functional activities are commenced 276. Depending on the activity the therapist may adjust various parameters for task or sub-task performance based on a visual assessment of the subject. For example, the therapist may change a threshold to encourage a subject to lean in a reach task. In other embodiments, the functional activity may be programmed to automatically adapt based on the context and performance of the subject in a particular set of tasks. Activities may be repeated 277 until completion 278. The performance of the subject during the functional activities may be stored for later evaluation and assessment in database 252.

FIG. 7c illustrates an example program control logic for defining and scripting motional tasks 290. In this example, the sensor thresholds as well as the vibrotactile feedback may be configured by the user or therapist for a particular activity or adapted for the specific needs of a subject. In multiple or complex tasks, the display may migrate from one mode to another as described hereinbefore. Tasks can be either set to default 281 or programmed to therapist defined parameters 285. The functional tasks can be chosen from a menu of standard activities 282 or be user defined 285. Multiple tasks may be concatenated and stored in the database 252. In user selected functional activity scripting, it may also be further desirable to select 285 timing, temporal, vibrotactile and display. Further, adaptation of the vibrotactile, display and timing thresholds may be selected 287. Adaptation criteria may be based on the subject's performance during the scripted motional activities and the subject achieving user defined metrics. For example, the pre-defined sensitivity thresholds for a functional activity, such as that described in FIG. 3, can be adapted at a user determined rate, based on how quickly and how often a vibrotactile display threshold is reached.

Figure 8:
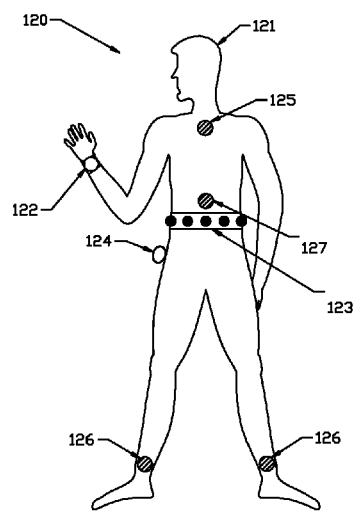
FIG. 8 illustrates another embodiment of a motional training system according to aspects of the present invention.

FIG. 8 shows a motional training system 120 on a subject 121. Sensors 125, 126 and 127 may be used to provide postural and gait information to an intelligent controller 124. The user can select various functional tasks and program modes via a wrist display 122 or in an alternate embodiment, the intelligent controller 124 may preempt the subject and recognize a limited set of functional activities. Sensor signal gesture recognition algorithms can be used for this purpose. User assistance during dynamic tasks is provided by a vibrotactile belt 123, controlled by the intelligent controller 124. In another embodiment of this invention, the transitional motion assistive device 120 may be configured with limited sensors or even without sensors. In this configuration the activities are cued in open loop i.e. the system acts to provide subject specific temporal, body referenced cues. In all embodiments, it is anticipated that the therapist programs subject specific parameters into the intelligent controller 124.

Figure 9:
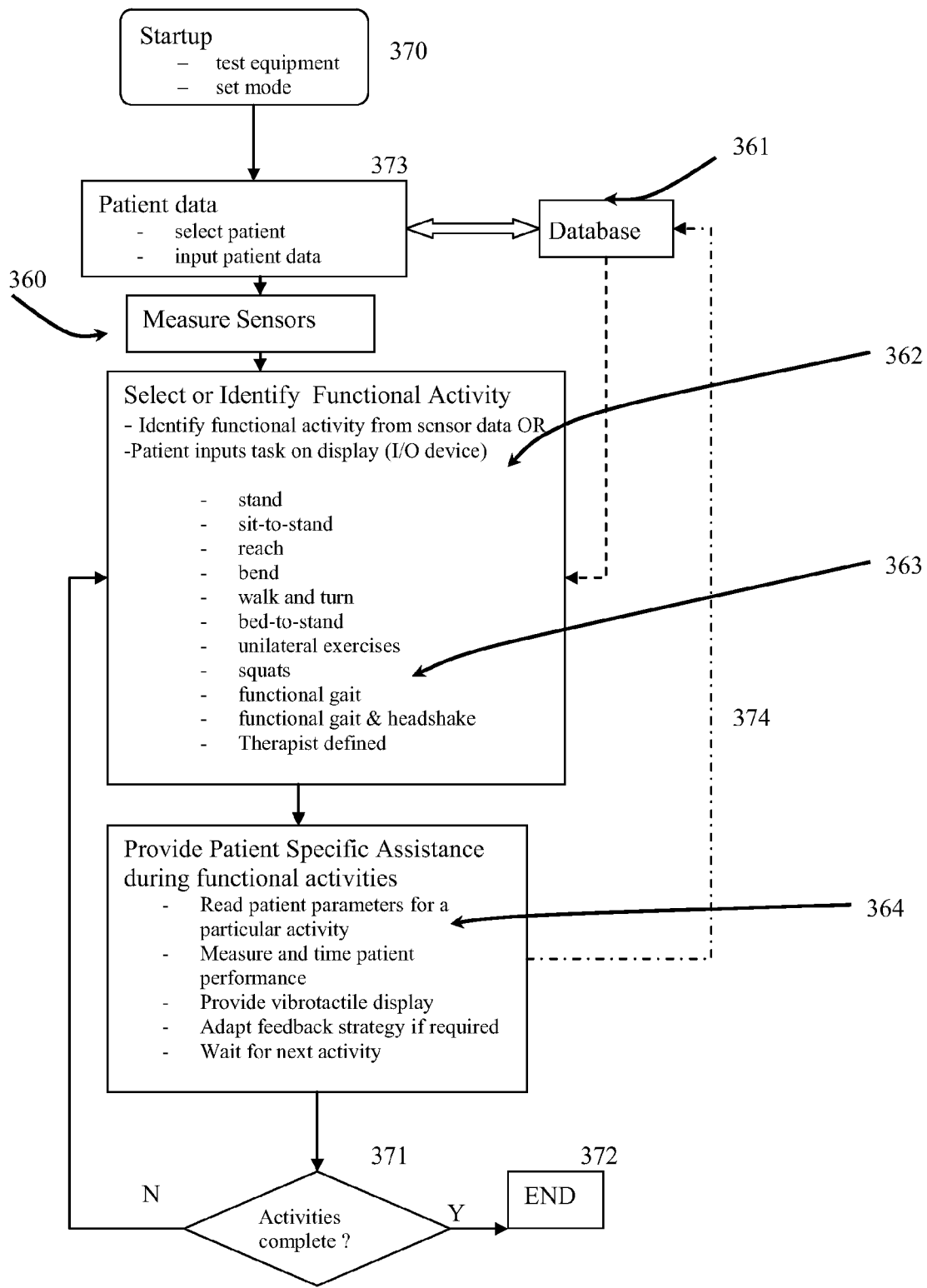
FIG. 9 illustrates an embodiment of a program flow for motional training according to aspects of the present invention.

FIG. 9 shows a program flow diagram 370 for motional training. The program flow includes the step 360 of measuring a suite of sensors to obtain body kinematics information, for example COP and COG. A database 361 is pre-programmed to contain subject data and subject specific parameters, such as timing data, subject needs, specific cueing information, adaptation and vibrotactile thresholds. The database 361 may also contain a set of gesture recognition parameters that are associated with a particular subject's movement parameters during previous motional activities. Subject functional movement tasks 362 may be either automatically recognized by the movement patterns determined from the sensor measurements 360 using the intelligent processor, or input by the subject or therapist using an interface device, for example a remote interface device 41 or wrist display 122 as described hereinbefore. Thus, the system knows what stage or state of the task 363, e.g., sit-to-stand, reach, walk and turn, or other pre-defined task, is being performed. The therapist enters subject specific parameters 373 into the database 361. The system thus uses the subject specific parameters stored in the database 361 to determine vibrotactile feedback display parameters. Vibrotactile guided motional assistance during specific tasks provided 364. The subject's performance during the functional activity tasks may also be measured and stored 374 in the database 361, allowing adaptive re-programming of the assistive steps as well as a record of subject compliance with the established protocols. Analysis of the database can be performed in real time by the therapist, or stored for subsequent downloading. Downloading and analysis may also be completed remotely using the internet and related approaches.

Figure 10:
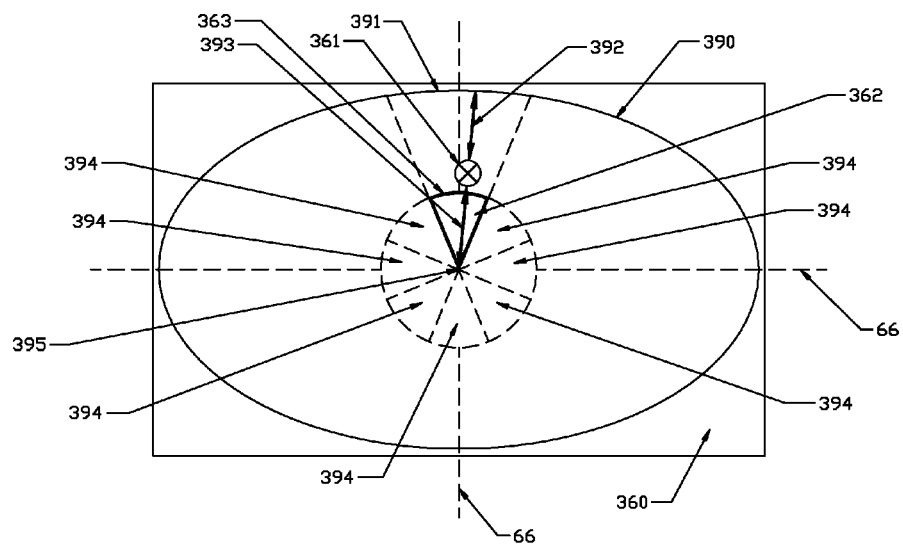
FIG. 10 illustrates an embodiment of this invention illustrating rate based variance and the implementation of rate based vibrotactile feedback.

FIG. 10 illustrates an alternate embodiment of this invention illustrating a method for calculation of rate based multi-sensory feedback in response to an attempt by the subject to perform predetermined motions. More specifically, FIG. 10 shows an example of a screen display 360 that may be shown by the intelligent controller 20 on the display monitor 30 referenced hereinbefore. The screen display 360 shows the center of pressure (COP) 361 of the subject 15 as determined via the force plates 11a and 11b. The COP and more specifically the ground reaction force presented by the subject 15 can also optionally be derived from combinational sensors, such as multiple inertial sensors, for example mounted at the base of the spine, used individually or in combination with force plate sensors. The example view 360 shows a training region that corresponds to a top down view of the area in which the subject is expected to perform a predetermined motion as a part of motional training on the force plates 11a and, or 11b. Accordingly, the screen display 360 may be used by the therapist and the subject 15 to monitor activity on the force plates 11a and 11b, and to provide visual feedback to complement the information provided by the vibrotactile feedback mechanism.

The view 360 shows a an inner zone comprising of a series of eight segments, or zones 394 around the subject 15, said zones being centered on axes 66 that are aligned with the subjects rest or zero (COP), or initial static posture position. For the purposes of illustration, a particular zone 362 is identified. In general, each zone 394 and zone 362, corresponds to a particular tactor on the array display. There are eight segments corresponding to typically eight actuators on the vibrotactile feedback mechanism 16. As described hereinbefore, the vibrotactile feedback mechanism 16 may be oriented such that one of the eight actuators 51 is centered on the front of the subject 15, while another actuator 51 is aligned with the spine, another actuator 51 is aligned with the right side, and another actuator 51 is aligned with the left side. Therefore, by way of example, the segment 362 shown in FIG. 10 may correspond with the actuator 51 on the front or belly area of the subject's torso. Each sector 394 maps to a corresponding spatial location on the tactor belt array and the axes of the force plate and subject are aligned with the display 360 axes 66.

In general, each segment includes an arc that represents an adjustable threshold for each corresponding vibrotactile actuator 51. By way of example, segment 362 will have an associated arc 363. The arc may be user or therapist set to be at any radius within a particular segment, thereby acting as a variable threshold up to a maximum location 390. In other words, the width of the segment 362 as well as the radius to the arc 363 (from the defined zero point 395) may be configured to set particular thresholds that determine when and how each of the actuators 51 are activated to provide feedback. Each segment arc may be set individually, or as a group. The length of the arc 363 represents a particular threshold which may be selected or modified during use so that information regarding movement of the subject relative to any thresholds provides useful information during motional therapy.

For example, as shown in FIG. 10, the COP 361 of the subject 15 has moved (by the subject leaning in a particular direct or through the effect of stepping motion) to a region beyond a segment 362 and arc 363, and the corresponding vibrotactile actuator 51 may be activated. Therefore there is a variance between the instantaneous location of the COP 361, and the preset threshold limits (as determined by that particular segment geometry) and the vibrotactile actuator corresponding to the sector location is activated.

In a particular feature of this invention, the instantaneous location of the COP 361 can be used to calculate the variance and successive measures of the COP 361 can be used to determine the rate of change of variance. The variance can be normalized by considering the length 393 from the zero point 395 to the instantaneous COP location 361 subtracted by the length from zero point 395 to the arc 363, and divided by the length 392 from the COP location 361 to the limit of maximum excursion 391 for a particular force plate or sensor configuration. For example, once the instantaneous COP 361 moves to a region beyond arc 363, within segment 362, the difference between length 392 and the length from the zero to arc 363 may be used to calculate a variance. Further, the rate of change of variance may be calculated by the derivative of this variance with respect to time. Well known techniques for calculating the derivative may use a number of successive samples divided by the time difference between these samples.

The normalized variance and rate of change of variance may be calculated by the intelligent controller 20, and in this embodiment of the invention, also be used to optimally apply rate based vibrotactile feedback to the subject 15 during motional training and consequent COP movement. For example, the normalized COP variance can be partitioned into discrete bands (or "bins") that correspond to a particular tactile feedback level. As the normalized variance increases, tactile feedback patterns can be that have salient characteristics that correspond to an increase in urgency. Pulse rate and tactile vibration amplitude (especially rise time) are our identified salient features that correspond to urgency. Typical pulse rates may have ON tone-burst lengths of between 10 and 800 ms. For example this activation may be via discrete linear limits; normalized variance<30% fires at a low pulse rate, 30%<normalized variance<60% fires at a medium pulse rate and 60%<normalized variance<100% fires at high pulse rate. In another example we activate tactors with tone-burst pulse repetition rates that depend on the normalized variance. If the COP location is greater than a preset threshold, normalized variance is used to modulate the tactor tone-burst repetition rate directly. For example an initial tactile pulse repetition sequence may start at a low pulse rate, and progress to a maximum pulse rate of at the highest normalized variance.

In another embodiment, the calculated normalized rate of change of variance may be used to optimally apply rate based vibrotactile feedback to the subject 15 during motional training and consequent COP movement. As the normalized rate of change of variance increases above a preset threshold, corresponding tactile feedback activations comprising of patterns can be activated. These tactile patterns have salient characteristics that correspond to an increase in perceived urgency. For example, therefore the rate of change of variance can modulate tactile activation via discrete linear limits; low normalized rate of change of variance fires at 250 ms on 50 off, medium normalized rate of change of variance fires at 250 ms on 25 ms off and high normalized rate of change of variance fires at 125 ms on 25 ms off. In another example we activate tactors with tone-burst pulse repetition rates that depend on the normalized rate of change of variance. If the COP location is greater than a preset threshold, normalized rate of change of variance is used to modulate the tactor tone-burst repetition rate directly. For example an initial tactile pulse repetition sequence may start at 400 ms on, 50 ms off, and progress proportionally to a maximum rate of 50 ms on 50 ms off at the highest normalized rate of change of variance.

Figure 11:
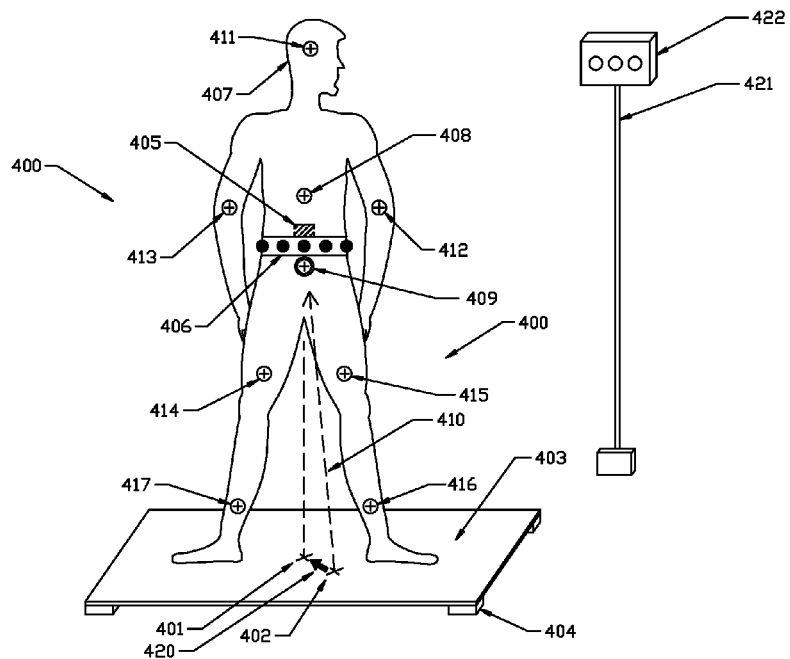
FIG. 11 shows an illustration of the means for calculating variance, or rate based variance, based on COP and COM measurement.

FIG. 11 illustrates an alternate embodiment of the invention 400, and more specifically a method for determining a variance between the at least one predetermined motion and the results of the attempt by the subject to perform the at least one predetermined motion. FIG. 11 describes the components associated with calculating such variance that is based on a force plate 403 derived COP 402, and a measurement of the ground projected center of gravity (COG) 401. The center of gravity (COG) 409 of a subject 407, is the net location of the subject's center of gravity in 3 dimensional space. The center of pressure (COP 402) is the weighted average of the location of all downward (action) forces acting on the standing surface. The COG 409 may be computed by making a weighted average of the COG's of each particular body segment (408, 411, 412, 413, 414, 415, 416,417) using a total body model, whereas COP 402 is measured using a force platform 403 with force sensors 404 between the plate and the ground surface (see for example, D. A. Winter (2005). Biomechanics and Motor Control of Human Movement. John Wiley & Sons, New Jersey).

The COP 402 represents the neuromuscular response to imbalances of the body's COG 409, i.e. when the COG 409 is displaced from the neutral axis of alignment, compensatory changes must be made in COP 402 to redirect the COG 409 back toward the neutral axis (or subject 407 zero as described hereinbefore). Such compensatory changes may be represented by a ground reaction force vector 410. These compensatory changes are related to time varying neuromuscular forces on the part of the subject. Further, the neutral axis of alignment depends on the motion to be performed. For example, in static steady stand, the neutral axis is typically a vertical line from base of support. In dynamic movements, such as sit to stand or reach, the neutral axis may depend on the stage of the movement. For example, as described hereinbefore, sit to stand may at least comprise of a stead sit stage with a neutral axis defined by stable sitting and a steady stand (goal state) with a new neutral axis defined by the stance. Therefore the ground projected center of gravity (COG) 401 represents a parameter that may be easily compared to COP 402 for the optimum calculation of variance between the at least one predetermined motion and the results of the attempt by the subject to perform the at least one predetermined motion.

One known prior art criterion for bipedal stability is that the body is able to maintain and control the position and motion of the total center of body mass (COG) 409 relative to the base of support. The COG in normal ambulation follows a trajectory in space. The analysis of the COG trajectory is often used to index balance performance during many functional tasks, for example, standing and walking.

Various methods are known in the art for the calculation of the COG 409 from the COP 402 data that include a kinematic model that derives the COG trajectory by low-pass filtering the COP 402, or double integrating the COP trajectory (see for example Betker et al. IEEE TRANSACTIONS ON NEURAL SYSTEMS AND REHABILITATION ENGINEERING, VOL. 17, NO. 6, DECEMBER 2009). Depending on the calculation method chosen, three axis load cell sensors 404 may be needed in order to resolve the ground reaction force 410 components.

Another known method of calculating the COG 409 by directly measuring the various body segment accelerations and inertias. For example, balance can be evaluated during standing tasks using a tri-axial accelerometer or preferably an inertial sensor 405. The COG 409 for a standing human is located approximately at the level of the second sacral vertebrae. If the inertial sensor 405 is placed on the back, close to this position, it will therefore approximately measure the trajectory of the combined COG 409. The inertial sensor 405 may also be preferentially located within the vibrotactile belt 406.

Figure 12:
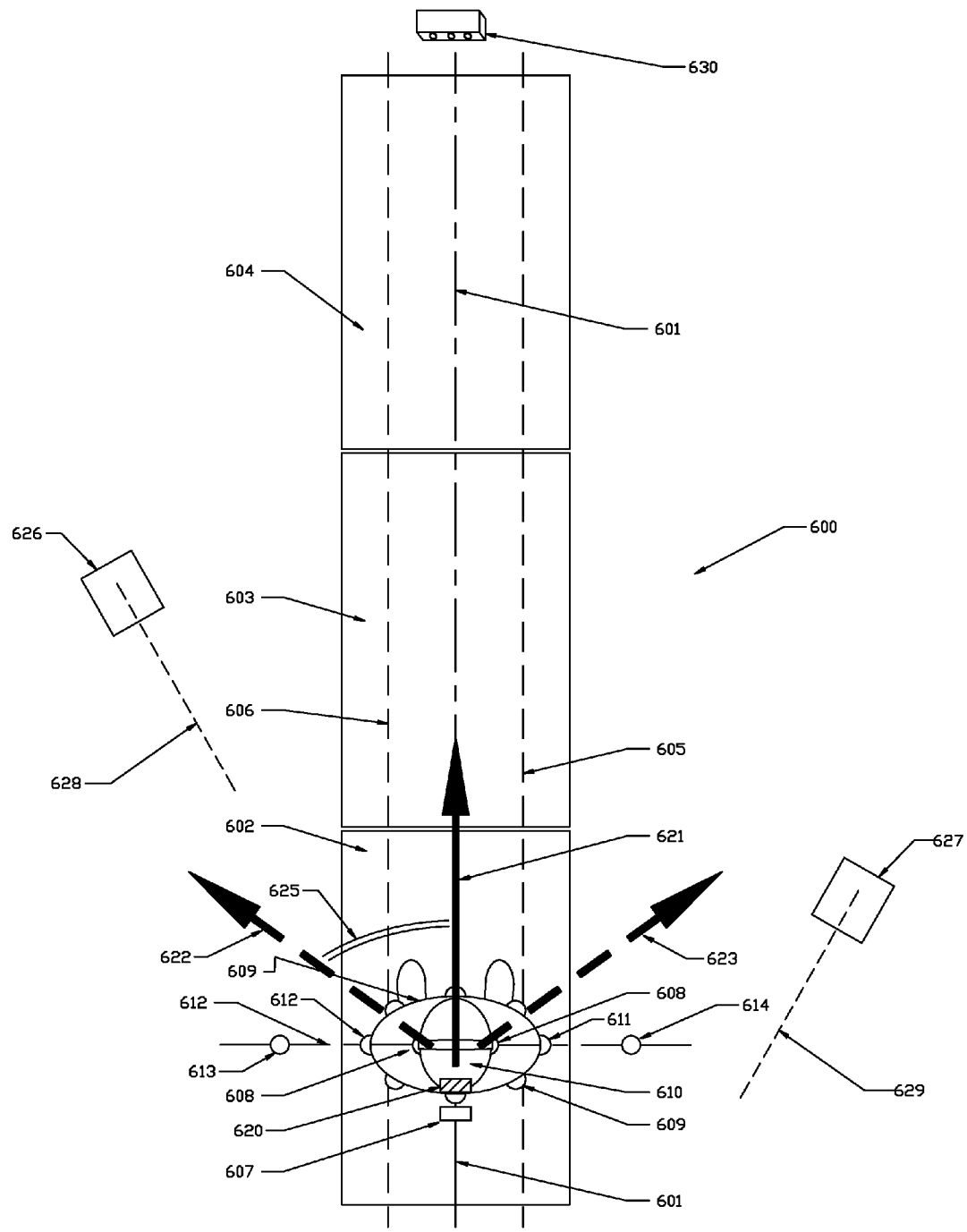
FIG. 12 illustrates an embodiment of this invention illustrating a functional gait task that may incorporate assessment measurements and feedback training.
Figure 13:
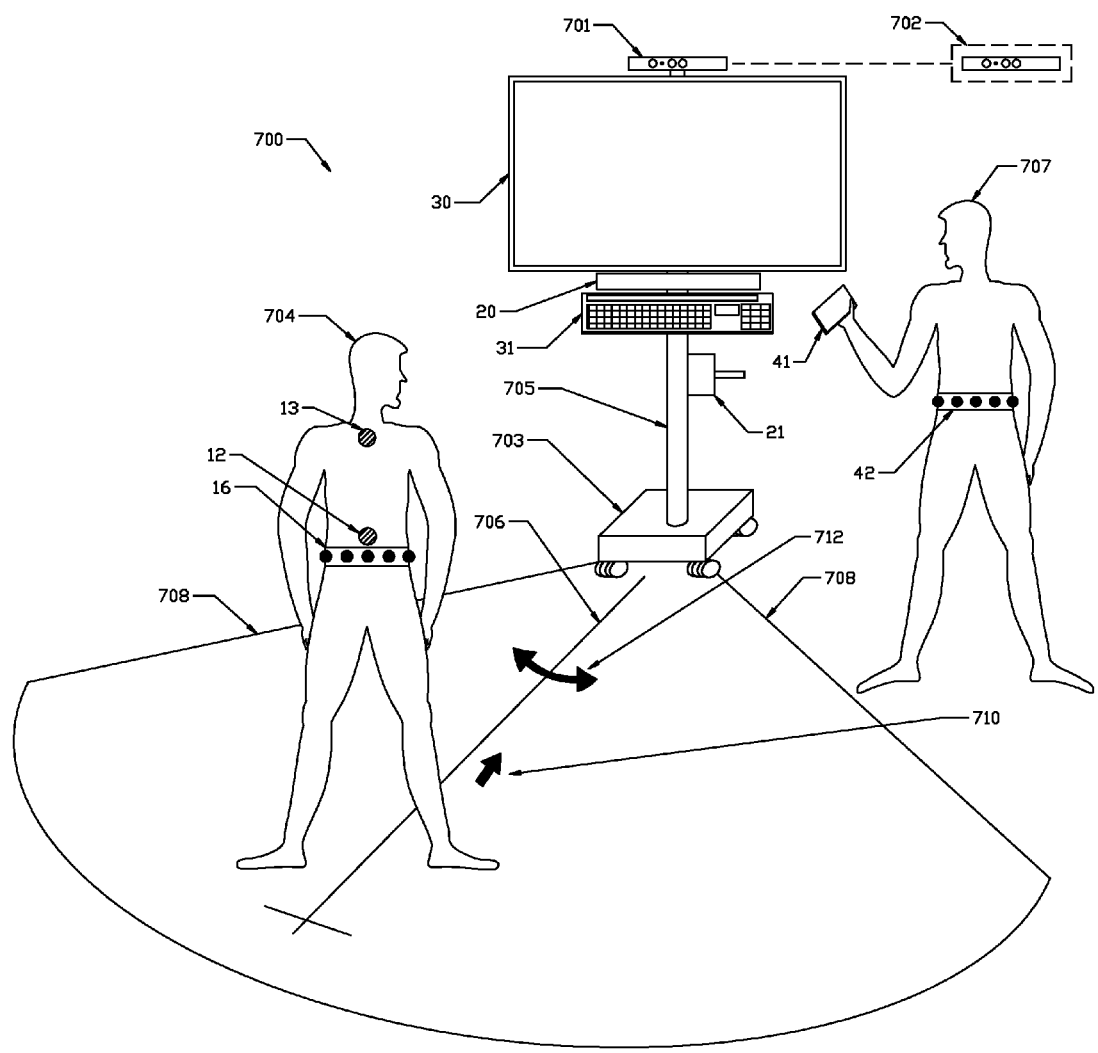
FIG. 13 illustrates an alternate embodiment of this invention illustrating one or more 3D camera sensors for motional training and assessment measurement.

In another embodiment, the ground projected COG 401 can be estimated using one or more 3D camera sensors 422 mounted on one or more stands or frames 421. As described hereinbefore, the 3D camera sensors 422 can estimate the COG 409 by computing a weighted average of the COG's of each body segment (408, 411, 412, 413, 414, 415,416,417) using a total body biomechanical model. The ground projected COG 401 can be estimated by projecting a line vertical (or perpendicular to the ground surface) from the COG 409 downwards, and determining the coordinates of the intersection of this line with the ground surface. This potentially avoids or reduces the need for inertial sensors or three axis load cells sensors in the force plate 403. Such 3D camera sensors can be used as shown in FIG. 11, FIG. 12 and FIG. 13, as a tool for the real time measurement of position of the subject 704.

In this embodiment, we preferentially calculate the variance during a postural activity for a subject by comparing the COP 402 to the calculated ground projected COG 401, and more specifically the difference between the COP 402 and the ground projected COG 401, which results in a variance vector 420. The variance vector 420 has a magnitude (given by its length) and a direction (given by the orientation of the vector in the plane of the ground surface).

For example, in another embodiment, the ground projected COG 401 can be approximated from the output of the inertial sensor 405, together with an estimation of the subject's 407 height (or more accurately, the length from the ground surface to the inertial sensor 405). For example, in steady stance, sway measured by inertial sensor 405 will measure the pitch, roll, yaw and 3 axis angular rates with respect to the axes of the sensor. Therefore the ground projected COG 401 is given by the sine of the associated angular sway multiplied by the length from the ground surface to the inertial sensor 405. In these calculations, the coordinates used in the inertial sensor 405 is the same as that used for the force plate 403.

In another example, the COP 402 can be measured by one or more force plates and the COG 401 calculated from the ground reaction force vector 410, or double integrating the COP trajectory (as described hereinbefore).

In another example, COG 409 can be measured using one or more 3D camera sensor 420 and the ground projected COG 401 calculated by using the intersection of a vertical line drawn from the COG 409 down to the surface of the force plate 403 to give the position of the ground projected COG 401. In these calculations, the coordinates used by the 3D camera sensor 422 are scaled and transformed to the same as that used for the force plate 403 (accounting for any errors in parallax seen by the 3D camera sensor).

The subject 407, during quiet stance, will typically use a postural strategy and neuromuscular compensation that will result in limit cycle oscillatory behavior between the COP 402 and ground reflected COG 401—thus the location of the COP 402 and ground projected COG 401 will vary. Thus the difference in location between the COP 402 and ground projected COG 401 is the variance vector 420, and can be used as a direct measure of the variance and direction of variance during a motional activity. For example during steady stand and static balance tasks it is desirable to minimize this variance. The direction of variance is calculated by considering the orientation of the variance vector 420 (between the COP 402 and the ground projected COG 401). The magnitude of this calculated vector is variance and the direction (in a coordinate frame referenced to the direction the subject is facing) indicates the direction in which the subject is moving towards.

For the example shown in FIG. 11, variance vector 420 has a direction relative to the force plate 403 and more specifically, the direction of the variance vector 420 may be defined relative to a coordinate system that is centered on the subject 407. The orientation of the subject 407 may be directly measured using inertial sensors on the subject's 407 torso, or using the data from 3D camera sensors 422 or by simply predetermining the orientation of the subject 407 in advance of the mobility training movement. Therefore, the direction of the variance vector 420 will also (in a coordinate frame referenced to the subject) correspond to one of eight previously described sectors 394, each sector having an associated vibrotactile actuator. In particular, the sensors determine the corresponding variance vector 420 and communicate this information to the intelligent controller 20. As discussed previously, thresholds may be visually defined on the display monitor via the intelligent controller 20 in terms of segments and arcs. In one embodiment, if the intelligent controller 20 determines that the variance vector magnitude exceeds a predefined threshold, a corresponding vibrotactile actuator in tactile belt 406 is activated to provide feedback to the subject 407 during an activity. The intelligent controller 20 will activate the tactor actuator corresponding to the direction of the variance vector 420. Thus, the subject 307 receives a vibrotactile stimulus, or feedback, when there is a significant variance between the location of the COP 401 and the ground projected COG 402. Similarly, the rate of change of variance may be also calculated for the variance vector 420 and used instead of, or in combination with, positional variance as described hereinbefore.

The calculation of variance by comparing the COP 402 to the calculated ground projected COG 401 provides a better estimate of subject variance or rate based variance during a task than either COP or COG alone. Further, predefined dynamic motional activities follow predictable patterns in the extent and direction of variance between the COP 402 and the ground projected COG 401. Therefore a feedback variance can be calculated by comparing the calculated vector 420 with predefined limits that are associated with a particular activity and stage of movement in an activity.

FIG. 12 illustrates particular features 600 of the invention; specifically training and computerized assessment during a series of functional gait tasks. It is well known that vision plays a major role in maintaining stability, both during stance and while undergoing movement such as walking. Balance dysfunction is often closely related to deficits in aspects of the sensory system, including vision. Rehabilitation may require specialist therapy that includes a series of head movements during dynamic motional activities. One of the most critical dynamic postural movement tasks is gait. Gait may be made more challenging by introducing tasks such as head movements during gait, changes in inertia with stepping, turns and obstacle avoidance. Further, narrowing the base of support such as stepping heel to toe greatly increases the task difficulty. It is noted that during this particular functional gait task, forward (anterior-posterior) COG motion is usually more controlled than medio-lateral (side to side) movement. Components of gait are also used in the prior art, as a basis for an assessment of the functional balance ability of subjects with balance dysfunction. However, previous approaches for assessment during functional gait stepping tasks have typically been based on a subjective score of the therapist or observer. Further assessment tasks are often masked by effects such as subject compensation and ceiling effects within the test construct that limit is applicability. Therefore it is desirable to provide an assessment system and method that overcomes these previous shortcomings.

Therefore particular features 600 of the invention include a system for the measurement of simultaneous postural signals together with head motion, or headshake, and a system for providing instantaneous feedback to the subject regarding the rate and extent of head motion during the activity.

The view 600 shows a top down depiction of one 602 or more (603 and 604) force plates that are aligned end-to end along a particular axis 601. The subject 610, by way of example, is shown aligned with axis 601. Axis 601 may also be shown on the force plate directly using a tape or the like. Each force plate 602, 603 and 604, measures the location of the subject's 610 center of pressure COP, thereby providing a measurement of the subject's postural signals during the functional gait activity. This information is input to an intelligent controller described hereinbefore.

In this functional movement task method, the subject 610 is instructed to perform a range of predefined motional activities that include gait. Gait may comprise of conventional tandem stepping, or stepping with a narrow base of support (heel to toe stepping). Gait activities are typically performed on the selected axis 601. The location of the COP, preset COP variance limits 605 and 606, are assessed by the intelligent controller. If the COP exceeds either limit, a variance, or rate of change of variance, is noted and an associated vibrotactile feedback may be provided to the subject 610. Vibrotactile feedback is particularly effective during therapy, providing the subject with real time, postural sway limit and directional (spatial) information. In this embodiment, it is preferable to provide vibrotactile feedback to only the sides of the subject's 610 torso. Therefore, although the subject may be wearing a belt with a larger array of tactors, typically only tactors 611 or 612 corresponding to the sides of the tactor belt 609 are used in these particular functional gait movement tasks. The activation of the tactors (modulation and vibration as described hereinbefore) is typically determined by the variance in COP above the preset thresholds 605 and 606. For example, if the COP moves from the axis 601 to a point beyond the preset variance limit 605, the tactor 611 will be activated (or modulated) until the subject 610 makes corrective motional movements to move the COP to a location between preset limits 605 and 606. The tactile feedback therefore acts to reduce the variance of the subject's COP and therefore to improve stability of the subject during functional gait training tasks. Similarly, the tactile activation, as described hereinbefore, may also be modulated by the extent and rate of change of variance, a variance in COG, ground projected COG, or in other examples a variance vector (determined from the difference between the COP and the ground projected COG).

In an alternate embodiment of this invention, a body worn inertial sensor 607 may be used to measure medio-lateral trunk sway and provide this information to an intelligent controller. In this case, the intelligent controller may use predefined medio-lateral trunk sway limits, or define the horizontal component of the medio-lateral trunk sway to be two limits 606 and 605. If the sway exceeds either limit, a variance is noted and an associated vibrotactile feedback is provided to the corresponding side of the subject 610. The vibrotactile feedback therefore acts to reduce the medio-lateral trunk sway variance and therefore improve the stability of the subject during gait.

Alternately the controller may use inertial sensor 607 information in combination with one or more force plate 602 sensors (603 and 604) information, to calculate the subject's medio-lateral sway together with the medio-lateral COP. In another configuration, the controller may use inertial sensor 607 information in combination with one or more force plate 602 sensors (603 and 604) information, to calculate the COG of the subject and calculate a medio-lateral variance, or rate of variance.

In another embodiment of this invention, one or more 3D camera sensors may be used to measure position and orientation (biomechanical features) of the subject 610. The 3D camera sensor 630 should preferably be located to be facing the subject 610 and aligned with the axis 601. This step co-aligns the camera axis with the activity area. The medio-lateral sway and characteristics of the subject 610 gait may be measured by the 3D camera sensor 630. Specifically, the COG or the trunk medio-lateral trunk sway angle can be calculated from the camera image field data by an intelligent controller that calculates the variance between the subject's actual COG motion or trunk sway angle and predetermined positional variance limits 605 and 606. The activation of the tactors (modulation and vibration information as described hereinbefore) is determined by the variance in COG or trunk sway angle above the preset thresholds 605 and 606. For example, if the COG moves from the axis 601 to a point beyond the preset variance limit 605, the tactor 611 will be activated (or modulated) until the subject 610 makes corrective motional movements to move the COG to a location between preset limits 605 and 606. Similarly, trunk medio-lateral sway angle is a highly sensitive indicator of instability and can be used by the intelligent controller as a measure of subject movement variance. For example, trunk segment medio-lateral sway angle excursions beyond preset limits will result in associated vibrotactile feedback on the corresponding side towards which the subject 610 may be leaning. Alternately, it is preferable in this embodiment, to combine both COG location and trunk angle and a composite predetermined limit for the determination of movement variance and the associated vibrotactile feedback.

The controller may also use this informational individually, or in combination with one or more force plate 602 sensor (603 and 604) information, or in combination with one or more inertial sensors, or in combination with both one or more force plates and one or more inertial sensors, to calculate the subject's medio-lateral sway or an estimation of the COG. Further, the controller may provide this information visually (using the visual display described hereinbefore), via the tactile modality (described hereinbefore) or a combination thereof.

In other embodiments, additional 3D camera sensors 626, 627 can be used to increase the functional movement operation range. For example, 3D camera sensors 626 and 627 can be located to be facing on axes 628 and 629 respectively. Axes 628 and 629 should be angled to face predominantly towards the primary axis 601 on which the subject will be required to complete functional gait tasks. The angle should be such that the 3D camera sensors do not interfere with subject 610 motion. The 3D camera sensors 627 and 626 should preferably be located at a height of 2 m and each 3D camera sensor should be approximately 4 m apart, thereby utilizing the full usable measurement range of the sensors. While this is a preferred configuration, it is not to be construed as a limitation of the system and method of the invention, as the location and orientation of 3D camera sensors is entirely a matter of preference of the user and may be affected by factors such as, for example, the space available for camera location.

For many subjects with balance dysfunction, especially those with vestibular deficit, head movements during gait may be difficult. Therefore, subjects may be inclined to only move their head within a narrow zone so as to preserve their stability. Further, during gait tasks, an injured subject may be inclined to restrict their head movements to periods in the gait cycle that are relatively stable. Heel to toe stepping involves a progression from stance, leg swing, front leg placement, landing and a weight shift from the back stance leg through to the forward leg (in a continuous cycle). During the stance transition, both legs are grounded potentially resulting in a perceived region of stability. Therefore injured subjects will likely only move their head during the stance transition and will be unwilling, or unable to move their head (and disrupt their vestibular system) at other points in the movement cycle. Similarly, stepping in general (for example, without a narrow base of support) has a gait cycle that is repetitive. Subjects with balance dysfunction, may introduce pauses in the gait cycle, or delay certain movements, or add in new transition states (for example additional steps) as a postural strategy during attempts to combine simultaneous head motion with gait. Simultaneous head movements may therefore be concentrated during certain states in the gait cycle and the gait cycle may be disrupted by head movements.

Therefore particular features of this invention include a system and method for guiding the subject regarding the extent and rate of head movement, and simultaneously measuring the resultant head movement together with the postural signals corresponding to the simultaneous gait task. This approach is further advantageous in that the functional activity is scalable in difficulty (eliminating any potential ceiling effects); difficulty may be increased by reducing the base of support (from standard gait to heel to toe stepping), by increasing the rate and extent of head movement, and by changing the head movement predetermined task from side to side movement sequences, to head back and chin to chest pitch movements (which disrupt different orientations in the vestibular system). Further, the dual nature of the task makes it more practically representative of typical functional tasks (and more difficult for the subject to "cheat") and the true functional balance capability of the subject.

It is an object of this invention to provide a system and method for measuring (assessing) the extent and nature of this particular type of balance dysfunction and also providing a system and means for assisting with rehabilitation. Therefore, in another embodiment of this invention, a head worn inertial sensor 620 is used to measure the head position (or head gaze) and provide this to the aforementioned intelligent controller. Specifically, FIG. 12 depicts a head gaze vector 621 that corresponds to a forward facing head direction of the subject 610. If the subject is instructed in a predetermined motional activity to move their head side to side, the head gaze vector will move through a range of angles during the side to side head movement. For example angle 625 will be measured between the forward gaze vector 621 and an extremity position 622. Similarly, another extremity position 623 is depicted for head rotations towards the right side of the subject. Extremity positions 622 and 623 can be preset and used as target goals for the subject head movement during a functional task. Further, angle 625 describes the rotational motion of the subject's 610 head during this motional activity.

Preferably, auditory feedback should be provided to the subject 610 when the gaze vector 621 reaches the target goal (extremity point). Audible feedback should be preferably provided through wireless headphones 608 that are worn by the subject 610, although a separate set of one or more discrete sound sources 614 and 613 may also be used in other embodiments, or other configurations such as a wired headset may be implemented. For those configurations utilizing one or more discrete sound sources, the sound sources should preferably be located on an axis 612 that closely corresponds with the medio-lateral axis of the subject 610. The auditory feedback is should produce a short tone (for example; 800 Hz, 50 ms duration, sound pressure level SPL 83 dBA) when the head rotation reaches a predetermined limit set by a predetermined angle 625 or extremity position 622 or 623. Preferably, auditory feedback should also correspond to the side towards which the head is turning. Therefore by way of example, auditory feedback should be presented to the headphone, or discrete sound source such as, for example and not by way of limitation, loudspeakers, corresponding to the left ear as soon as the head is rotated past limit 622 and similarly to the right ear when the head is rotated past the predefined limit 623 that may be set for the associated right side.

Other motional training head movements such as up down (nodding), diagonal and ear to shoulder can also be implemented in this activity. Collectively, side-to-side, up-down and diagonal head movements are referred to as headshake. In each headshake movement, the head worn inertial sensor 620 provides a measurement of the head position and orientation which can be used by an intelligent controller to calculate the relative head position and provide the subject with feedback guidance via an associated auditory tone once a predefine head positional threshold has been reached. Vibrotactile feedback should be preferentially given during these head movement therapy tasks based on the variance, or rate of chance of variance, between the instantaneous COP and preset limits.

In alternate embodiments of this invention, tactile feedback or visual feedback can be provided to the subject 610 when the gaze vector 621 reaches the target goal (extremity point). Preferably, tactile feedback should also correspond to the side towards which the head is turning. Therefore by way of example, tactile feedback should be presented to the tactor 612 corresponding to the left side as soon as the head is rotated past limit 622 and similarly to the right side 611 when the head is rotated past the predefined limit 623 that may be set for the associated right side. While this is described configuration, it is not to be construed as a limitation of the system and method of the invention, as the location and numbers of tactors used in this mode of feedback is entirely a matter of preference of the user.

It is desirable during functional gait assessment and rehabilitation activities for subject to be simultaneously moving their head during gait. It is a particular feature of this invention that the intelligent controller can also present the required rate of the head movement to the subject in advance of the activity; playing an auditory pattern of tones (or alternately, tactor tone-burst pulses) at a rhythmic rate. The therapist may determine the rhythmic rate based on the subjects abilities and increase this to increase task difficulty. Suitable rhythmic rates are from 0.1 to 3 Hz. The subject should then, during the activity, move their head to an extent and rate such that the resultant auditory feedback (as a result of head motion reaching the predetermined limits) mimics that pattern of rhythmic tones. For example, an activity may have preset threshold limits that are preset to be 30 degrees from forward gaze 621, and require the subject to move their head at 1 Hz in a side to side headshake activity. The subject may be further required to move by stepping heel to toe along axis 601 whilst simultaneously moving their head. This provides a dual task which adds to the cognitive load for the subject 610. Further the headshake motion perturbs the vestibular system which makes the sensory motor integration task considerably more difficult. The rate of headshake provides a simple parameter that can also be modulated to increase or decrease this particular functional gait task difficulty. Therefore the therapist can control the functional gait task by manipulating the goals (headshake rate, head rotation limits, plane of rotation and stepping) for the functional activity.

In other embodiments of this invention, one or more 3D camera sensors 630 can be used to measure the head orientation signals and provide this to the aforementioned intelligent controller. Further, one or more 3D camera sensors may be used to simultaneously measure and determine the biomechanical features of the subject 610 who is performing gait within the sensing field of one or more 3D camera sensors. Therefore, this embodiment allows for a simpler sensor configuration with an increase in image processing requirements on the intelligent controller.

This invention 600 is particularly useful as an assessment measurement tool for measuring the functional balance abilities of a subject. Multiple gait tasks are known to be reliable and accurate indicators of behavior functional ability. However, prior-art efforts to assess performance during such complex gait activities rely on human observations and subjective scoring. Therefore it is also an object of this invention, to provide measures that consist of multiple items that are to be summarized clinically into a composite score using computer based (automated scoring). For example, headshake may be simultaneously measured together with COP excursion during a dynamic gait task with associate head movement. The COP sway may be compared to pre-set limits or scored proportional to preset constant that are based on subject height, foot size and age). Excursions due to unplanned trips and falls may similarly be evaluated from the collected data and presented as a variance to be included in a score. The score may be made up of multiple tasks (as described in the list hereinbefore), each assessed individually. Therapist and patient instructions are further automated and provided using a computer. This is described in further detail below.

FIG. 13 illustrates another embodiment of a motional training system 700 according to aspects of this invention. The motional training system 700 is operated by a therapist 707 to provide motional training for a subject 704. As described previously, in an example application, the motional training system 700 may be employed to treat various balance disorders in the subject 704. As shown in FIG. 13, the subject 704 is situated within the field of view 708, of one or more 3D camera sensors 701 and 702. The field of view 708 may have a central axis 706 which may indicate an area and orientation where the subject should preferably locate. A vibrotactile feedback mechanism 16 as well as optional inertial sensors 12 and 13 may be mounted on, or coupled to, the subject 704 as described hereinbefore. Meanwhile, another vibrotactile feedback mechanism 42 may be mounted on the therapist 707.

In general, the motional training system 700 may be operated with an intelligent controller 20, which may be any processing device, such as a conventional desktop computer, that can execute programmed instructions (or system software) provided on media, such as computer-readable memory. A visual display monitor 30 and an optional keyboard interface 31 may be connected to the intelligent controller 20 to provide a user interface. The therapist 707 may also operate aspects of the motional training system 700 via a remote interface 41 as shown in FIG. 13. The remote interface could be a touch screen, keypad or the like, connected via a wireless interface to the intelligent controller 20.

The 3D camera sensor 701, the vibrotactile feedback mechanism 16, and the optional inertial sensors 12 and 13 may communicate with the intelligent controller 20 via conventional wired or wireless connections. For example, 3D camera sensor 701 may communicate directly to the intelligent controller 20 using a wired connection, such as a conventional universal serial bus (USB) connection or the like. Meanwhile, a wireless data connection 21, such as Bluetooth or the like, shown in FIG. 13 may allow the intelligent controller 20 to communicate with the vibrotactile feedback mechanism 16 and the optional inertial sensors 12 and 13. In addition, the remote interface device 41 may also use a wireless interface to connect to other components of the motional training system 700. In general, wireless communications may be particularly suitable for components of the motional training system 700 that must move easily with the subject 704 or the therapist 707. In other embodiments, the components (visual display monitor 30, intelligent controller 20, keyboard interface 31 and wireless data connection 21) may be integrated within one composite unit, for example a touchscreen all-in-one computer.

In other embodiments, additional 3D camera sensors 702 may be connected to the intelligent controller 20, thereby extending the combined sensor usable measurement range or increasing the overall motional training system 700 accuracy.

The 3D camera sensor (701) provides an instrument for measuring the position, body sway as well as the biomechanical joint positions and angles of the subject 704 who is standing within the field of view 708 of the sensor. Specifically the body segments (such as the torso or limbs) are identified from the 3D camera sensor image field (sensor output) and their position and orientations can be individually tracked by the intelligent controller 20. Therefore the center of gravity (COG) for the subject can be readily calculated in real time at up to the framing rate of the 3D camera sensor (for example 30 frames per second). The 3D camera sensor (701) may in certain embodiments also be used to measure head orientation signals of the subject 704 as described hereinbefore.

Similarly, biomechanical features such as the trunk angle and trunk position can be measured by the intelligent controller 20 and the dynamic movement strategies of the subject 704 can be estimated. For example, it is well known in prior art that static stance movement strategies may use ankle torque (or ankle strategy) or hip flexure (hip strategy) or a combination of the two during balance. Therefore, if the body segments are known at each frame instant (and the feet positions are fixed), the balance strategy can be identified. If the upper and lower body segments move in the same direction or in phase with one another, then ankle strategy is being used and the human stance can be modeled as an inverted pendulum. Since the amount of force that can be generated by the muscles surrounding the ankle joint is relatively small, this strategy is generally used to control standing sway through a very small range of motion. In contrast to the ankle strategy, the hip strategy involves activation of the larger hip muscles and is used when the center of gravity must be moved more quickly back over the base of support as the speed or distance of sway increases. When using the hip strategy, the upper body moves in a direction opposite to that of the lower body. Subject's 704 may interchange between these postural control strategies (for example after instruction, environment). However, if the center of gravity is displaced beyond a maximum limit, or the speed of sway is so fast that the hip strategy is insufficient to maintain stability, then stability can only be maintained by finding a new base of support, for example by stepping.

Therefore one or more 3D camera sensor 701 and 702 are advantageous as the complete motion and postural strategy employed by the subject 704 can be determined by the intelligent controller 20 and displayed on the screen 30 or therapist 707 remote interface 41.

3D camera sensor 701 (and 702) will result in a sensor field of view 608 with a defined vertical, horizontal and depth range (this will be determined by the height of the sensor, the design and environment). Typical 3D camera sensors may have reasonable horizontal and vertical accuracy, but will have less precision in depth. Further, areas that are located behind opaque objects in the field of view of the sensor cannot be resolved. Therefore it is beneficial to use two or more 3D camera sensors 701 and for example 702, that are located with different, intersecting fields of view, to provide a more accurate and robust calculation of the biomechanical joint positions and angles of the subject 704 who is standing within the field of view 708 of the sensor. For example, 3D camera sensor 701 may be placed on a wheeled 703 stand 705, with another 3D camera sensor 702 located distal to the first, thereby orientating the sensors with different aspects and orientations to the subject. The subject orientation 710 and example movement 712 with respect to each of the sensors can be detected and classified by the intelligent controller 20. Thereby a method for extracting the most accurate features from each sensor (for example placing greater priority on measurements that are not depth related) may be used by the intelligent controller. The measurements of the subject 704 biomechanical features (such as COG, joint angles and positions) are therefore combined from multiple sensors (mapping, scaling and weighting as necessary) into a more precise composite system based measurement.

Although the sensors used in some embodiments may employ the use of one or more 3D sensors 701 and 702, the embodiment of FIG. 13 also employs the optional inertial sensors 12 and 13. As illustrated in FIG. 13, the inertial sensor 12 may be mounted proximate to the center of gravity (COG) of the subject 704, i.e., in the area of the lower back of the subject 15. The inertial sensor 12 may be mounted according to any suitable arrangement. For example, the inertial sensor 12 may be incorporated with a belt or garment worn by the subject 704. Alternatively, the inertial sensor 12 may be incorporated into the vibrotactile feedback mechanism 16 worn by the subject 704. Meanwhile, the optional additional inertial sensor 13 may be mounted higher on the upper body of the subject 704, for example at the back of the neck proximate to the top of the spine. The inertial sensor 13 may be incorporated in a garment or accessory worn by the subject 704. Accordingly, the inertial sensor 12 provides information regarding the orientation and motion of the COG, while the inertial sensor 13 second sensor provides information regarding the orientation and motion of the upper body of the subject 704.

In another embodiment of the motional training system 700, one or more 3D camera sensors 701 and 702, optionally combined with one or more inertial sensors 12 and 13, measure appropriate body orientation and approximate the location of the center of gravity for the subject 704. As described hereinbefore, sensor information is used together with knowledge of various functional activities to predict and compare the actual body response and posture during various stages of each particular functional task.

The intelligent controller 20 can be operated to drive the vibrotactile feedback mechanism 16 to provide feedback to the subject 704 during motional training. This feedback may include spatially oriented and body-referenced information, temporal information, information based on sequences or patterns of pulses, as well as information based on vibration frequency. As described previously, the spatially oriented and body-referenced information may include directional information based on the location and urgency of the vibrotactile stimulus.

The therapist 707 may interface with the intelligent controller 20 and system software via the screen display 30 and the keyboard 31. However, to make it easier for the therapist 707 to monitor and assist the subject 15 during the motional training, the therapist 707 may alternatively use the remote interface 41 to control aspects of the motional training system 700. In addition, because the vibrotactile feedback mechanism 16 provides information directly to the subject 704 undergoing motional training, the motional training system 10 may provide the therapist 707 with a similar vibrotactile feedback mechanism 42 as shown in FIG. 13 so that the therapist 707 can monitor the information that the subject 704 is receiving.

The operation of the motional training system 700, is similar to that described hereinbefore; the subject 704 attempts to move according to one or more motions defined as a part of the motional training, e.g., moving from a sitting position to a standing position to test static balance. These predetermined motions may make up all or part of a functional activity. One or more 3D camera sensors 701 and 702 measure the attempt by the subject 704 to move according to the predetermined motions. In particular, the 3D camera sensors determine corresponding subject 704 physical position in space and any associated movements. The intelligent controller 20 then determines the subject 704 COG, biomechanical joint positions and angles. In one embodiment, if the intelligent controller 20 determines that the COG has moved beyond any threshold, the intelligent controller 20 activates the actuator corresponding to the segment. Thus, the subject 704 receives a vibrotactile stimulus, or feedback, when there is a variance between the location of the COG and the predetermined movement threshold.

Figure 14:
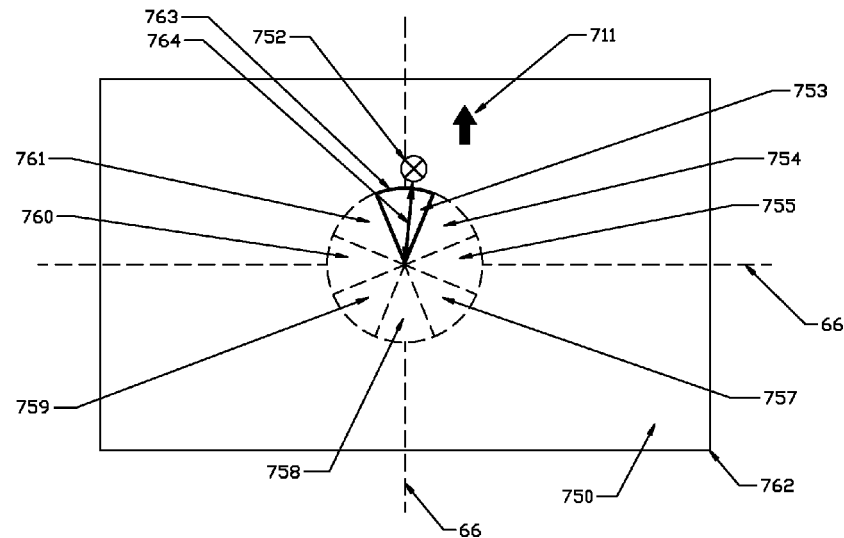
FIG. 14 shows an example of a screen for visual and vibrotactile feedback during motional training according to aspects of the present invention.

FIG. 14 illustrates a screen display 762 that may be shown by the intelligent controller 20 on the display monitor 30 or used to describe the method for calculating a variance during a particular functional movement task. The screen display 762 provides a view 750 that shows the center of gravity (COG) 752 of the subject 704 as determined from the 3D camera sensor 701, or derived from combinational sensors such as the optional additional 3D camera sensors 702, force plates and inertial sensors described hereinbefore. The view 750 also shows a training region that corresponds to a physical area within the field of view 708 of the 3D camera sensors (701), in which the subject is expected to perform a predetermined motion as a part of motional training. Accordingly, the screen display 762 may be used to monitor activity by the subject 704, and to provide visual feedback to complement the information provided by the vibrotactile feedback mechanism 16. In addition, the screen display 762 may be employed to set parameters or thresholds for operation of the vibrotactile feedback mechanism 16.

As FIG. 14 further illustrates, the view 750 also shows information relating to the vibrotactile feedback mechanism 16. In particular, the view 750 shows a series of eight segments, or zones, 753, 754, 755, 757, 758, 759, 760, and 761. In this view, the subject 704 is facing in a direction indicated by the arrow 711 in FIG. 14. Therefore the subject coordinate frame is also aligned with the visual display view 750 and axes 66. Each segment corresponds to an actuator 51 on the vibrotactile feedback mechanism 16. In the embodiment of FIG. 14, there are eight segments corresponding to eight actuators on the vibrotactile feedback mechanism 16. As described previously, the vibrotactile feedback mechanism 16 may be oriented so that one of the eight actuators 51 is centered on the front of the subject 704, another actuator 51 is aligned with the spine, another actuator 51 is aligned with the right side, and another actuator 51 is aligned with the left side. Therefore, the segment 753 shown in FIG. 14 may correspond with the actuator 51 on the front of the subject, the segment 758 may correspond with the actuator 51 aligned with the spine, and segments 755 and 760 correspond with the actuators 51 on the right and left sides, respectively.

By way of example, segment 753 includes an arc 763 that represents an adjustable threshold for the corresponding vibrotactile actuator 51. In other words, the width of the arc 763 as well as the length of the segment 753 may be configured to set thresholds that determine when a particular body reference actuators 51 will be activated to provide feedback. If, for example, the COG 752 of the subject 704 moves to a region beyond a segment 753 and arc 763, the corresponding vibrotactile actuator 51 may be activated. In other words, when there is a variance between the determined location of the COG 752, a corresponding vibrotactile actuator is activated. The length vector 764 between the zero origin and the COG 752 can be used by the intelligent controller 20, as a variable to compare to the arc 732 (associated with the segment in which the length vector 764 is located, in this case 753). Similarly, in another example a vibrotactile actuator 51 may be activated until the COG 752 of the subject 704 moves to a corresponding region beyond a segment 753 and arc 763. Thus, the segments 753 and arc 763 may correspond to thresholds that define the boundaries for movement by the subject 707. The thresholds are selected so that information regarding movement of the subject relative to these thresholds provides useful information during motional therapy. It is noted that movement of the COP 752 can be caused when the subject sways, and movement by foot or other significant movement is not required. As such, the example embodiment illustrated by FIG. 14 can assess static balance.

During an example operation of the motional training system 700, the subject 704 attempts to move according to one or more motions defined as a part of the motional training, e.g., moving from a sitting position to a standing position to test static balance. These predetermined motions may make up all or part of a functional activity. The 3D camera sensor 701 (and optional sensor 702) react to the attempt by the subject 704 to move according to the predetermined motions. In particular, the 3D camera sensor 701 (and optional sensor 702) determine corresponding movement of the COG 752 and communicate this information to the intelligent controller 20. As discussed previously, thresholds may be visually defined on the display monitor 30 via the intelligent controller 20 in terms of corresponding segment arcs. In one embodiment, if the intelligent controller 20 determines that the COG 752 has moved beyond any of the segments and past any of arcs, the intelligent controller 20 activates the actuator 51 corresponding to that corresponding segment. Thus, the subject 704 receives a vibrotactile stimulus, or feedback, when there is a variance between the location of the COG 752 and the segments and the arcs.

Before operation, the COG 752 may be initially zeroed, or reset, to align the axes 66 and the segments 61 over the COP 752. However, the axes 66 may also be zeroed after a subset of the predetermined motions during the motional therapy. The therapist 707 may zero the axes 66 and segments (753, 754, 755, 757, 758, 759, 760, and 761), for example, via the therapist remote interface 41 while monitoring the subject's attempt to perform a set of predetermined motions. The motional training system 700 allows the subject 704 to sequentially move from one region to another according to the set of predetermined motions, e.g. from a sitting position to a standing position and so on. Zeroing allows to each region, i.e., a subset of the predetermined motions. Otherwise, the thresholds would only apply to the set of predetermined motions as a whole. In other embodiments, the intelligent controller automatically recognizes each movement stage and performs appropriate axis zeroing. For example, in sit to stand, sensor information together with the intelligent controller recognizes sitting from the location of the COG (using for example COG height and its proximity to chair). As the subject starts to transition to standing, the COG position and location can be used to identify the various stages of motion (as described hereinbefore) and adjust the thresholds (segments) and zero the axes at the appropriate stages. Therefore, an adaptive intelligent controller recognizes the state of the subject during a motional activity, and adjusts the movement feedback threshold and axes.

Figure 15:
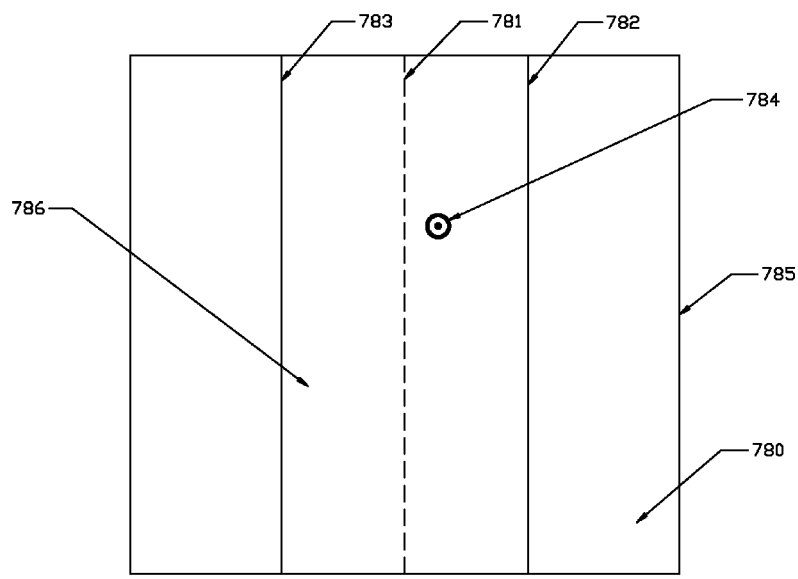
FIG. 15 shows an example of a visual display that illustrates the features associated a functional gait training or assessment task.

FIG. 15 illustrates a simple screen display 785 that may be shown by the intelligent controller 20 on the display monitor 30 or used to describe the method for calculating a variance during a particular functional gait task. The screen display 785 provides a view 780 that shows the center of gravity (COG) 784 of the subject 704 as determined from the intelligent controller 20, the 3D camera sensor 701, or derived from combinational sensors such as the optional additional 3D camera sensor 702, force plates and inertial sensors described hereinbefore. The view 780 also shows a target stability region 786 (between limits 783 and 782) in which the subject is expected to perform a predetermined gait as a part of motional training. Accordingly, the screen display 785 may be used to monitor activity by the subject 704, and to provide visual feedback to complement the information provided by the vibrotactile feedback mechanism 16. In addition, the screen display 785 may be employed to set parameters or thresholds for operation of the vibrotactile feedback mechanism 16.

As FIG. 15 further illustrates, the view 780 also shows information relating to the medio-lateral sway limits 783 and 782 which represent the predetermined maximum (goal) limits of lateral sway for a particular gait or dynamic motional task. As described hereinbefore, a particular objective of functional gait training is to limit the extent of lateral sway of the subject 704. The intelligent controller 20 assesses the instantaneous location of the COG, the preset medio-lateral sway variance limits 783 and 782, and provides vibrotactile feedback to the subject by vibrating and modulating the tactors corresponding the to the associated sides of the tactor belt, activation being determined by the variance in COG beyond the preset thresholds 783 and 782. Tactile activation, as described hereinbefore, may be modulated by the extent and rate of change of variance.

The screen display 785 may be also used as visual feedback to the subject while performing the functional gait task by displaying the information in real time on the screen 30. The center 781 or sway goal may be additionally displayed as a reference. The objective during functional gait task with visual feedback, may be to minimize the sway and therefore keep the COG 784 as close to the goal center 781. In other examples, the goal 781 may be moved to another location within a stable area 786 to encourage motional activity towards a new set of goals. This screen display 785 therefore provides a simple intuitive visual feedback construct from which the subject can observe their actual medio-lateral COG location during intended motion and provide voluntary corrective motional strategies that keep the COG within a predefined range.

Figure 16:
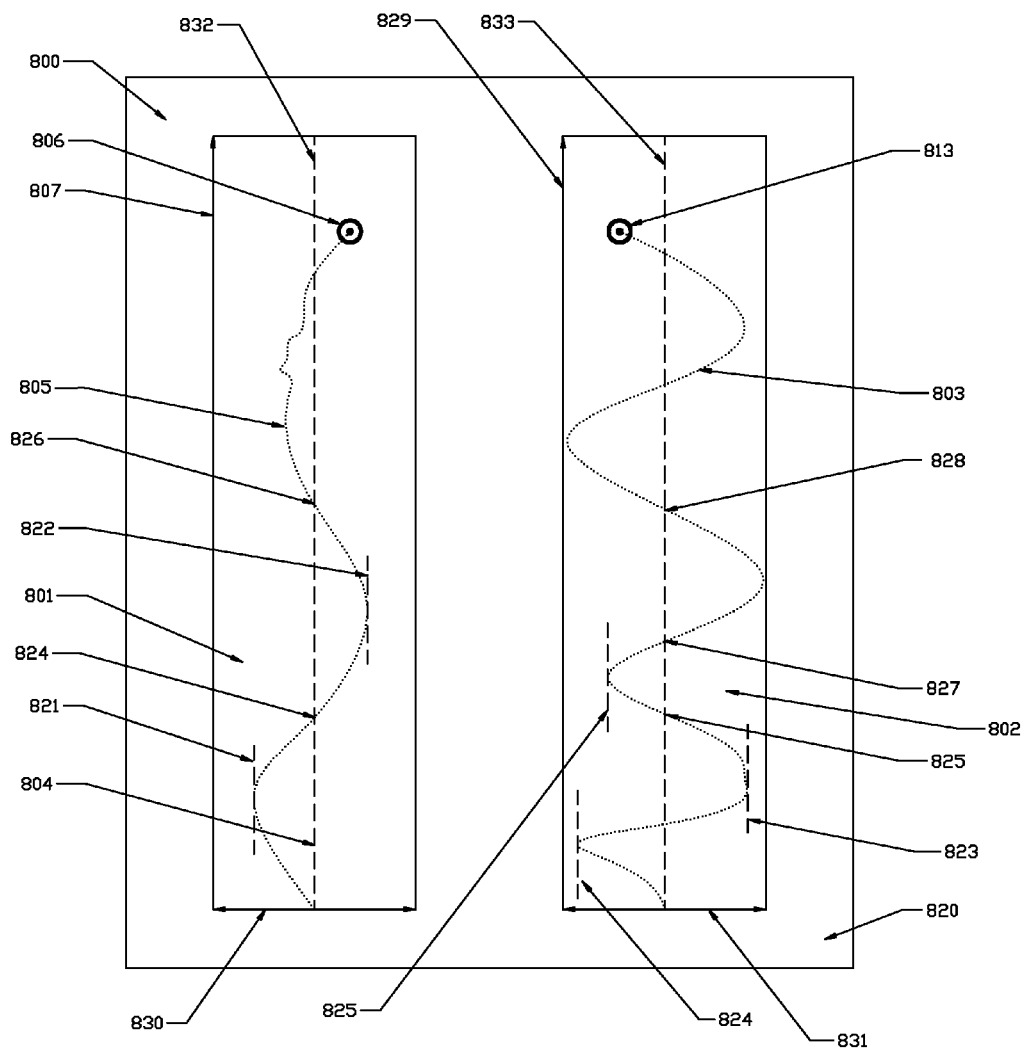
FIG. 16 shows and example of a visual display that illustrates aspects of a functional gait task.

FIG. 16 illustrates a screen display 820 that may be shown by the intelligent controller 20 on the display monitor 30 as a summary of the subject performance during, or after completion of, a particular functional gait task. View 800 shows one or more traces, 801 and 802, that illustrate signals produced by hereinbefore described sensors, in response to an attempt by the subject to perform said predetermined task. For example, trace 801 may preferably correspond to the COP (or COG) variation with time and position, and trace 802 may preferably correspond to the headshake angle with time and position. The biomechanical features and head orientation signals used in the determination of COG, COP and headshake angle, may be derived from one or more sensors, or sensor combinations as described hereinbefore. In this invention, the subject is instructed to perform a range of predefined motional activities that include gait (stepping, heel to toe stepping, turns and the like) together with simultaneous head movements. As described hereinbefore, motional gait activities are usually performed along a predefined axis, on which the subject attempts orientate their functional gait task. In certain examples, this axis may be depicted as a line or tape on the ground, or a series of lines indicating target boundaries for the subject movement during a particular task. Typical head movements may include headshake, where the head is rotated through various orientations (for example, side to side) through a range of head rotation angles between predefined extremity positions. Various sensor configurations can be used for the determination of the COP (or COG) as well as the headshake angle and have been described hereinbefore.

Trace 801 and 805 signals therefore describe aspects of the actual performance of the subject during the functional gait task. Each signal component will also be associated with one or more limit parameters that are defined for the functional gait task. If the signal exceeds said limit parameter, a variance occurs. As described hereinbefore, the variance may be used to provide feedback; for example, auditory feedback regarding headshake limits, or in the case of a COP (or COG) variance, a corresponding body referenced tactile transducer can be used to alert the subject to correct his or her posture. In this invention, the variance between the parameter (the expected value) and the measured signal may also be preferably used as a measure of the subject's performance.

Trace 801 shows a first axis 807, corresponding to time and another axis 830 that corresponds to medio-lateral COP (or COG) position. The mid-point or zero (as calibrated by the system or therapist to be the mean position), corresponds with a second axis 832 that is preferably also aligned with the axis on which the intended motion of subject is to be performed. Display 820 shows the instantaneous COP (or COG) position 806 together with a signal graph 805 trace or record, of the previous COP (or COG) data samples. The graph 805 will typically show sway characteristic features (of the subject and functional motion task). These features typically resemble an oscillatory pattern in the medio-lateral axis 830 that corresponds to an associated sway with each step in the gait.

Characteristic features in the signal trace 805 can be identified by the intelligent controller, for example, the maximum of the graph 821 and 822 can be identified together with one or more zero crossing points 824 and 826. Further, if a limit parameter is identified (for example a maximum medio-lateral COP excursion), and the signal exceeds said limit parameter, a variance occurs.

In another embodiment of this invention, trace 801 may show a first axis 807, corresponding to the subject's relative anterior-posterior COP (or COG) position, or distance along a predefined functional gait task axis and a second axis 830 corresponding to medio-lateral COP (or COG) position. Therefore the subject may start at an initial location close to axis 830 and in a predefined functional gait movement, step along an axis displayed on trace 801.

Characteristic features in the gait can be identified from trace 801. For example, the gait velocity, acceleration, jerk, energy in the frequency domain, cycle by cycle step length (for example the first stepping phase of gait 804 is shown from the graph 805 origin to the first zero crossing 824), rhythm and medio-lateral sway extent (difference between maximum 821 and 822) can be readily extracted from the data in trace 801.

In further r embodiments of this invention, trace 801 may be made up one or more characteristic features such as; instantaneous weight, medio-lateral shear, anterior-posterior shear, left and right leg biomechanical features (such as ankle angle, velocity, torque, knee angle, hip angle), trunk biomechanical features (such as angle, velocity) and COG height.

Trace 802 shows a first axis 829 corresponding to time and second axis 831 that corresponds to headshake angle. The mid-point or zero (as calibrated by the system or therapist to be the subject forward facing or neutral head position), corresponds with an axis 833 that is preferably also aligned with the axis (or direction in which the subject is facing) on which the intended motion of subject is to be performed. Display 820 shows the instantaneous headshake angle 813 together with a graph 803 trace or record, of the previous angle data samples. The graph 803 will typically show characteristic features associated with intended (and unintended) head motion of the subject while they are completing aspects of this functional motion task. Characteristic features in the signal trace 803 can be identified by the intelligent controller, for example, the maximum (824, 825 and 823), can be identified, together with one or more zero crossing points 825, 827 and 828. Further, if a limit parameter is identified (for example a maximum medio-lateral COP excursion), and the signal exceeds said limit parameter, a variance occurs. Characteristic features in signal trace 803 will typically correspond to an oscillatory variation in angle that corresponds to an intended head movement (headshake). According to aspects of this invention, the intended oscillatory rate may be set by the system or therapist, preferably using auditory (or tactile) feedback and a target rhythm (or goal metronome tempo) as described hereinbefore. The target rhythm may be set within certain limits to increase or decrease task difficulty. For example, a target rate of less than 0.5 Hz for headshake is relatively easy. Increasing the rate from 0.5 Hz to 1 Hz may increase the task difficulty. Headshake of up to 3 Hz is achievable in certain healthy subjects, however subjects with balance dysfunction will perturb their vestibular sensory system during this task, which may be limiting. Therefore, headshake rate provides a useful parameter for therapists to modulate task difficulty; starting with a low rate and increasing this as the subject is able to master the task. Therefore, modulation of headshake rate can also be a useful feature in an assessment method; various gait tasks trials can be performed with different preset headshake rates. Similarly, the predetermined headshake limits may also be used to modulate the task difficulty; increasing the limit angle (as described hereinbefore) and maintaining the same headshake rate will required the head to be rotated with higher angular velocities (which will increase the task difficulty).

In another embodiment of this invention, trace 802 may show a first axis 829, corresponding to the subject's relative anterior-posterior COP (or COG) position, or distance along a predefined functional gait task axis and a second axis 831 corresponding to head orientation angle. Therefore the subject may start at an initial location close to axis 831 and in a predefined functional gait movement, step along an axis as displayed on trace 801 and simultaneously, the head angle 813 at location will be displayed on trace 802.

In this invention, two or more predetermined tasks may be performed simultaneously by the subject. Further, one or more variance sensor signals may be produced in response to an attempt by the subject to perform either of these predetermined tasks, and used to assess the subject's ability to perform the predetermined tasks, or more generally, as an assessment of the subjects functional balance ability.

The headshake movement task is performed simultaneously with aspects of functional gait, therefore trace 801 and 802 will be related (for example, axes 832 and 833 may be of the same measurement kind and represented using same units). Further, there are components of the intended movements (for example, gait stepps in trace 801 and head movements in trace 802). These intended components are displayed displayed as signal features on trace 805 and 803, and can be identified by the intelligent controller. There may also be unintended movements in both the gait and in the intended head movement that will also be shown as signal features on trace 805 and 803. In other words, instability in gait may result in unintentional changes in the head movement of the subject and vice versa.

Therefore, characteristic features and variances in the gait can be identified by the intelligent controller and displayed on a combinational screen display 820. For example, particular characteristic features such as the gait velocity, cycle-by-cycle step length (for example the first stepping phase of gait 804 is shown from the graph 805 origin to the first zero crossing 824), rhythm and medio-lateral sway extent (difference between maximum 821 and 822) can be readily extracted from the data in trace 801. These signal parameters can be compared to limit parameters to determine one or more variance signals. The variance signals may further have state characteristics assigned to them based on the time or stage in the functional activity that they occurred in (as described in more detail hereinafter).

Similarly, characteristic features and variances in the head movement can be identified by the intelligent controller and displayed on a combinational screen display 820. For example, particular features such as the maximum head movement angle (for example 824 in one head direction and 823 in the other), velocity, period between head movements (for example the headshake 803 trace periodicity is shown on graph 803 as axis 833 zero crossings 825, 827, 828), rhythm and head movement extent (difference between maximum 824 and 823) can be readily extracted from the data in trace 802. The headshake oscillation can also be readily obtained from either the cycle by cycle zero crossings (for example 825, 827, 828), wavelet analysis or a Fourier transform of the data 803. These signal parameters can be compared to limit parameters to determine one or more variance signals. More specifically, a first variance may occur if the headshake signal parameter is less than a first limit parameter, and a second variance may occur if the signal parameter is more than a second limit parameter. For example if head movements during this task are restricted, the resultant headshake signals for may be less than a predetermined limit, resulting in a first variance. This variance may occur at one or more attempts by the subject to move their head through a range of motions. Similarly, the headshake rate or oscillation may be less than a predetermined limit, resulting in a first variance. This variance may occur during one or more attempts by the subject to move their head through a range of motions. A second variance may occur if the headshake rate or oscillation is more than a predetermined limit. Similarly, a related measure is periodicity which may be measured as the time between zero crossings. A first variance may occur if the period is less than a predetermined limit and a second variance may occur if the period is more than a predetermined limit. Another embodiment measures the time period where head orientation is less than predetermined thresholds. This time period indicates minimal headshake (or lack of head movement). In this case a variance occurs if this time period is greater than a predetermined limit setting. Variance signals may further have state characteristics assigned to them based on the time or stage in the functional activity that they occurred in (as described in more detail hereinafter).

As described hereinbefore, any discontinuities in the biomechanical features related to gait, and the head orientation signals (related for example to headshake oscillation) may be indicative of an attempt to regain balance. Therefore, in one embodiment of this invention, the periodicity of the head movement may be extracted from a time history of recorded data (signal traces) using signal processing, for example autocorrelation. A first variance may occur if the period is less than a predetermined limit and a second variance may occur if the period is more than a predetermined limit. This variance can then be used to compile a score for a particular activity. By way of example, if the headshake data is uncorrelated and discontinuous, it would receive a lower numerical score than headshake data that is periodic and continuous. Other methods, such as cross-correlation, spectral coherence may also be used for determining the correlation between traces 801 and 802, generally termed a correlation measure. In each case the correlation measure can be compared to a predetermined limit. If the correlation measure is greater than a predetermined limit, a variance will occur. The variance can be used as a score for the subject's capability in this functional gait task and therefore used as an assessment of balance dysfunction.

Measured and identified characteristic features will be associated with the predetermined intended task and a variance may exist between ranges of intended features versus the actual subject data. As described hereinbefore, this variance may be also derived into a rate of variance, and may be used as a basis during therapeutic activities to calculate thresholds and conditions for vibrotactile feedback to be presented to the subject. In another embodiment of this invention, the calculated variance is used as a direct measure of the subjects movement error during the act of completing the task and can therefore be used as a score of the subjects performance. More specifically, the greater the number of variance occurrences and the higher the magnitude of cumulative variance the poorer the performance. Therefore, the intelligent controller records the number of variances in one or more signal characteristics, and calculates the magnitude of each of the variances. These may be displayed as normalized scores and averaged over several attempts on the part of the subject to complete the functional gait task. Further, the variances and scores may be stored in the system and used and a session by session measure of the subjects performance during motional training.

Instability may also be correlated with the associated stage of gait shown in 801. Therefore it is advantageous to further break the recorded data and features into phases of the gait cycle. It is known that gait will have swing and stance components for each limb. Gait is typically symmetrical for healthy subjects (see for example, M. Nordin and V Frankel, Basic Biomechanics of the Musculoskeletal System, $3^{rd}$ Edition, 2001). In one gait cycle, each individual leg goes through a complete step cycle; each leg's step cycle is phase shifted relative to the main gait cycle. The step cycle is broken into two main stages—the support stage (foot on ground) and transfer stage (foot in the air). The amount of time a leg spends in the support stage is the support duration and likewise, the amount of time spent in contact with the ground is the transfer duration. The stage of gait can be estimated from the COP (or COG) location 806 or in other embodiments, features of trunk sway angle. The transfer phase during gait is associated with the subject moving such that their COP (or COG) shifts towards the support limb. Thus the intelligent controller can identify the various phases of gait from the data 805 shown in trace 801. In particular, aspects such as the state (stand, initial step, transfer, support, terminal swing, end stand) should be cyclical and can be used as a measure of subject performance. For example, subjects with balance dysfunction may tend to be discontinuous in their gait cycle, moving between stand, initial step and terminal step without ever transitioning to a repetitive transfer and support cycle. Further correlation analysis between traces 801 and 802 can be measured by the intelligent controller. Specifically Fourier transform and coherence analysis can be performed as an estimate of the power spectra of each of these signals.

The biomechanical features related to gait, and the head orientation signals in healthy subjects will be correlated, while subjects with balance dysfunction will have aspects of noise in one or more of the signals. Therefore, non-linear analysis can be used to compare the signal parameters and score the amount of correlation (or lack of correlation). These scores can be combined into a graphical or numerical score associated with that particular task activity and the attempt on the part of the subject to perform a predetermined task.

In other embodiments of this invention, the characteristic states of the gait cycle can be identified by the intelligent controller and associated with a particular time range (or medio-lateral position). Variances in any of the signal characteristics during the motional task can then be assigned state characteristics assigned to them based on the gait stage or state. Therefore, it the variance can be scored based on number of variance occurrences and the variance magnitude (as described hereinbefore), and additionally weighted based on the stage of gait. For example, variances that occur during gait states that are known to be stable may be weighted with a higher weighting than other (more stable) gait stages. In other examples, the head motion signals may be classified according to the stage of the gait. This classification may be visual including this information on the graph (as color changes and the like), or used to calculate signal processing features as described hereinbefore.

This invention provides a method for the clinical assessment of balance dysfunction in a subject. In a particular functional gait motional trial, the subject may be instructed to complete aspects of gait in combination with head movements. Multiple measures of the subject performance may that consist of multiple items that are to be summarized clinically into a composite score using computer based (automated scoring). Features of headshake are simultaneously measured together with features of the COP (or COG) excursion during a dynamic gait task with associated head movement.

The score may be determined by the determination of a variance or number of variances in signals. The variances may be further classified into the number of occurrences and the magnitude of the variance. The variance may be further classified by the stage or state that the variance occurred, said state being related to the subjects gait. In yet a further embodiment of the invention, vibrotactile stimulation may be provided to the subject during the assessment of functional gait in order to provide a disruptive stimulus. Such stimulation may be used to further assess balance and dysfunction in a subject. In this embodiment, the vibrotactile stimulation is provided by placement of one or more vibrotactile actuators on the body of the subject under assessment. The therapist may then choose the level and frequency of the applied disruptive stimulation. The number of actuators, level of stimulation, frequency of stimulation, and like parameters are within the control of therapist and are not to be construed as a limitation of the invention. The therapist may choose the stage or gait state in which to provide the vibrotactile stimulation. Preferably, this should coincide with stages in the gait cycle that may be perceived to be unstable (such as during swing strides as described hereinbefore). Disruptive stimulation can correspond to the stride side or in certain cases be contra-lateral (opposite side).

Features of the COP (or COG) sway may be compared to pre-set limits or scored proportional to preset constant that are based on subject height, foot size and age). In other embodiments, the combined variance between the features of COP (or COG) and headshake angle may be used to compile a score. Excursions due to unplanned trips and falls may similarly be evaluated from the collected data and included in a score. The score may be made up of multiple gait movement trials, multiple variance measures, each assessed individually and combined with various weightings into a totals score.

The rate of headshake provides a simple parameter that can be modulated to increase or decrease the functional gait task difficulty. Headshake rate may be provided during therapy or trial activities from auditory feedback related to the actual head movement attained. A headshake rate goal may be preferentially provided by an auditory rhythm. Multiple gait movement trials, with vibrotactile feedback and without vibrotactile feedback can compared to assess the dependence of the subject on feedback. In other embodiments, vibrotactile feedback may be presented during functional movement trials as a confounding, or perturbation during various stages of the activity. The confounding vibrotactile stimulation may be further synchronized to specific stages of the gait cycle (for example during the initiation of gait swing). While various embodiments in accordance with the present invention have been shown and described, it is understood that the invention is not limited thereto. The present invention may be changed, modified and further applied by those skilled in the art. Therefore, this invention is not limited to the detail shown and described previously, but also includes all such changes and modifications. Specifically, when the word "therapist" is used herein, its meaning includes any person who is operating the system and method of invention which may be a technician, physician, system operator, or the like; thus the use of the term "therapist" has wide meaning and is not to be construed as limiting the invention to use only by therapists.

What is claimed is:

1. A method for assessing disequilibrium and movement and balance disorders of a subject, comprising:

a. providing at least one sensor selected from the group consisting of at least one force plate, at least one three dimensional camera, and at least one inertial sensor;
    b. positioning a subject within a sensing field of said at least one sensor;
    c. identifying a predetermined headshake task for said subject to perform while positioned in said sensing field, said predetermined headshake task being defined by at least one headshake parameter selected from the group consisting of angular rate of headshake and angular extent of headshake;
    d. identifying a predetermined motional task for said subject to perform while positioned in said sensing field, said motional task being defined by at least one motional task parameter;
    e. receiving at least one headshake sensor signal produced by said at least one sensor in response to an attempt by said subject to perform said predetermined headshake task and said predetermined motional task simultaneously, wherein said headshake sensor signal represents at least one headshake variance between a subject's actual performance of said predetermined headshake task and said at least one parameter of said headshake task;
    f. receiving at least one motional task sensor signal produced by said at least one sensor in response to an attempt by said subject to perform said predetermined motional task; wherein said motional task sensor signal represents at least one motional task variance between a subject's actual performance of said predetermined motional task and said at least one motional task parameter of said motional task;
    h. using said at least one headshake variance and said at least one motional task variance to assess a subject's ability to perform said predetermined motional task.

2. The method of claim 1 in which said predetermined motional task is further defined as a functional gait task.

3. The method of claim 1, further comprising the step of providing a cueing signal selected from the group consisting of auditory, vibrotactile, and visual to a subject during said attempt by said subject to perform said predetermined headshake task, said cueing signal signaling an angular extent of said headshake.

4. The method of claim 3, in which said step of providing a cueing signal is further defined as said cueing signal being applied to said subject in a direction corresponding to a direction of said headshake.

5. The method of claim 2, further comprising the step of providing a cueing signal selected from the group consisting of auditory, vibrotactile, and visual to said subject during said attempt by said subject to perform said predetermined motional task and said headshake task, said cueing signal signaling an angular extent of said headshake.

6. The method of claim 5, in which said step of providing a cueing signal is further defined as said cueing signal being applied to said subject in a direction corresponding to a direction of said headshake.

7. The method of claim 1, further comprising the step of providing a cueing signal selected from the group consisting of auditory, vibrotactile, and visual to said subject during said attempt by said subject to perform said headshake task and said motional task, said cueing signal signaling a desired angular rate of said headshake.

8. The method of claim 1 further comprising the step of recording and displaying said at least one headshake variance during said attempt by said subject to perform said predetermined headshake task and said predetermined motional task.

9. The method of claim 1 further comprising the step of determining a correlation between said motional task variance and said headshake variance.

10. The method of claim 2 further comprising the step of comparing a functional gait periodicity and a headshake periodicity.

11. The method of claim 1 further comprising the step of determining a numerical score based upon said at least one headshake variance.

12. The method of claim 2 further comprising the step of determining a numerical score based upon said at least one headshake variance.

13. The method of claim 3 further comprising the step of determining a numerical score based upon said at least one headshake variance.

14. The method of claim 4 further comprising the step of determining a numerical score based upon said at least one headshake variance.

15. The method of claim 1 further comprising the steps of determining a rate of change of said at least one motional task variance, and determining a numerical score based upon said rate of change of said at least one motional task variance.

16. The method of claim 7, in which said step of providing a cueing signal is further defined as said cueing signal being applied to said subject in a direction corresponding to a direction of said headshake.

17. The method of claim 2, further comprising the step of providing a cueing signal selected from the group consisting of auditory, vibrotactile, and visual to said subject during said attempt by said subject to perform said predetermined motional task and said predetermined headshake task, said cueing signal signaling an angular rate of said headshake.

18. The method of claim 17, in which said step of providing a cueing signal is further defined as said cueing signal being applied to said subject in a direction corresponding to a direction of said headshake.

19. A method for assessing disequilibrium and movement and balance disorders of a subject, comprising:

a. providing at least one sensor selected from the group consisting of at least one force plate, at least one three dimensional camera, and at least one inertial sensor;
b. positioning a subject within a sensing field of said at least one sensor;
c. identifying a predetermined headshake task for said subject to perform while positioned in said sensing field, said predetermined headshake task being defined by at least one headshake parameter selected from the group consisting of angular rate of headshake and angular extent of headshake;
d. identifying a predetermined motional task having at least one motional task parameter for said subject to perform while positioned in said sensing field,
e. receiving at least one headshake sensor signal produced by said at least one sensor in response to an attempt by said subject to perform said predetermined headshake task; wherein said headshake sensor signal represents at least one variance between a subject's actual performance of said predetermined headshake task and said at least one headshake parameter;
f. receiving at least one motional task sensor signal produced by said at least one sensor in response to an attempt by said subject to perform said predetermined motional task; wherein said motional task sensor signal represents at least one variance between a subject's actual performance of said predetermined motional task and said at least one motional task parameter; and
g. providing a feedback selected from the group consisting of auditory, vibrotactile, and visual to said subject in response to said at least one headshake variance during said subject's simultaneous performance of said predetermined headshake task and said predetermined motional task; and
h. using said at least one motional task variance to assess said a subject's ability to perform said first predetermined motional task.

* * * * *